(12) United States Patent
Abreu

(10) Patent No.: US 11,596,348 B2
(45) Date of Patent: Mar. 7, 2023

(54) WEARABLE DEVICES CONFIGURED TO SUPPORT MEASUREMENT AND TRANSMISSION APPARATUS

(71) Applicant: GEELUX HOLDINGS, LTD., Tortola (VG)

(72) Inventor: Marcio Marc Abreu, Aventura, FL (US)

(73) Assignee: GeeLux Holdings, Ltd., Tortola (VG)

( * ) Notice: Subject to any disclaimer, the term of this patent is extended or adjusted under 35 U.S.C. 154(b) by 0 days.

(21) Appl. No.: 15/085,452

(22) Filed: Mar. 30, 2016

(65) Prior Publication Data
US 2016/0287165 A1 Oct. 6, 2016

Related U.S. Application Data

(60) Provisional application No. 62/140,989, filed on Mar. 31, 2015.

(51) Int. Cl.
*A61B 5/00* (2006.01)
*A61B 5/01* (2006.01)
*A61B 5/021* (2006.01)

(52) U.S. Cl.
CPC ............ *A61B 5/441* (2013.01); *A61B 5/0002* (2013.01); *A61B 5/0015* (2013.01); *A61B 5/6806* (2013.01); *A61B 5/6826* (2013.01); *A61B 5/01* (2013.01); *A61B 5/021* (2013.01)

(58) Field of Classification Search
CPC ............................ A61B 5/6806; A61B 5/6826
See application file for complete search history.

(56) References Cited

U.S. PATENT DOCUMENTS

| 4,407,295 | A | | 10/1983 | Steuer et al. | |
|---|---|---|---|---|---|
| 5,964,701 | A | * | 10/1999 | Asada | A61B 5/002 128/903 |
| 6,567,990 | B1 | * | 5/2003 | Spitznagle | A61B 5/0492 2/160 |
| 6,846,106 | B1 | * | 1/2005 | Chen | A61B 5/01 340/407.1 |
| 2001/0000526 | A1 | * | 4/2001 | Gopinathan | A61B 5/0002 600/300 |
| 2002/0198443 | A1 | | 12/2002 | Ting | |
| 2003/0125629 | A1 | * | 7/2003 | Ustuner | A61B 8/00 600/459 |
| 2004/0156012 | A1 | | 8/2004 | Jannard et al. | |
| 2004/0178970 | A1 | | 9/2004 | El Sayed et al. | |
| 2004/0193211 | A1 | * | 9/2004 | Voegele | A61B 5/6826 606/205 |
| 2004/0225217 | A1 | * | 11/2004 | Voegele | A61B 5/6843 600/439 |

(Continued)

OTHER PUBLICATIONS

International Preliminary Report on Patentability dated Oct. 12, 2017, in corresponding PCT Application No. PCT/US16/25000, 9 pp.

(Continued)

*Primary Examiner* — Shirley X Jian
(74) *Attorney, Agent, or Firm* — Studebaker & Brackett PC

(57) ABSTRACT

Devices that take a novel approach to parameter measurement and output or transmission of signals, medicine, heat, etc. These devices are compact, versatile, relatively inexpensive, and require minimal training to be effectively used. These devices can be configured as interchangeable devices incorporated into a wearable article or device.

10 Claims, 15 Drawing Sheets

(56) References Cited

U.S. PATENT DOCUMENTS

| | | | |
|---|---|---|---|
| 2004/0242976 A1* | 12/2004 | Abreu | A61B 5/0008 |
| | | | 600/315 |
| 2008/0081963 A1* | 4/2008 | Naghavi | A61B 5/01 |
| | | | 600/301 |
| 2008/0300488 A1* | 12/2008 | Schutz | A61B 5/6826 |
| | | | 600/459 |
| 2010/0111763 A1* | 5/2010 | Kahn | A61B 5/02042 |
| | | | 422/400 |
| 2011/0218436 A1* | 9/2011 | Dewey | A61B 8/14 |
| | | | 600/443 |
| 2012/0083710 A1* | 4/2012 | Yarden | A61B 5/6802 |
| | | | 600/549 |
| 2012/0143018 A1* | 6/2012 | Skidmore | A61B 5/02 |
| | | | 600/301 |
| 2012/0287041 A1* | 11/2012 | Bucholz | G06F 3/0317 |
| | | | 345/157 |
| 2013/0030257 A1 | 1/2013 | Nakata et al. | |
| 2013/0158365 A1* | 6/2013 | Chey | A61B 5/14503 |
| | | | 600/595 |
| 2014/0336492 A1 | 11/2014 | Lin | |
| 2015/0296111 A1* | 10/2015 | Rajan | A61B 1/00016 |
| | | | 348/68 |
| 2015/0342521 A1* | 12/2015 | Narita | A61B 5/4893 |
| | | | 600/546 |
| 2016/0100799 A1* | 4/2016 | Muniz | A61B 5/6806 |
| | | | 600/388 |

OTHER PUBLICATIONS

Notification of Transmittal of the International Search Report and the Written Opinion of the International Searching Authority; PCT/US2016/025000 dated Jul. 1, 2016.

International Search Report dated Jul. 1, 2016, in corresponding PCT Application No. PCT/US16/25000, 2 pp.

Written Opinion dated Jul. 1, 2016, in corresponding PCT Application No. PCT/US16/25000, 7 pp.

An Examination Report mailed by the Australian Patent Office dated May 23, 2018, which corresponds to Australian Patent Application No. 2017200974.

* cited by examiner

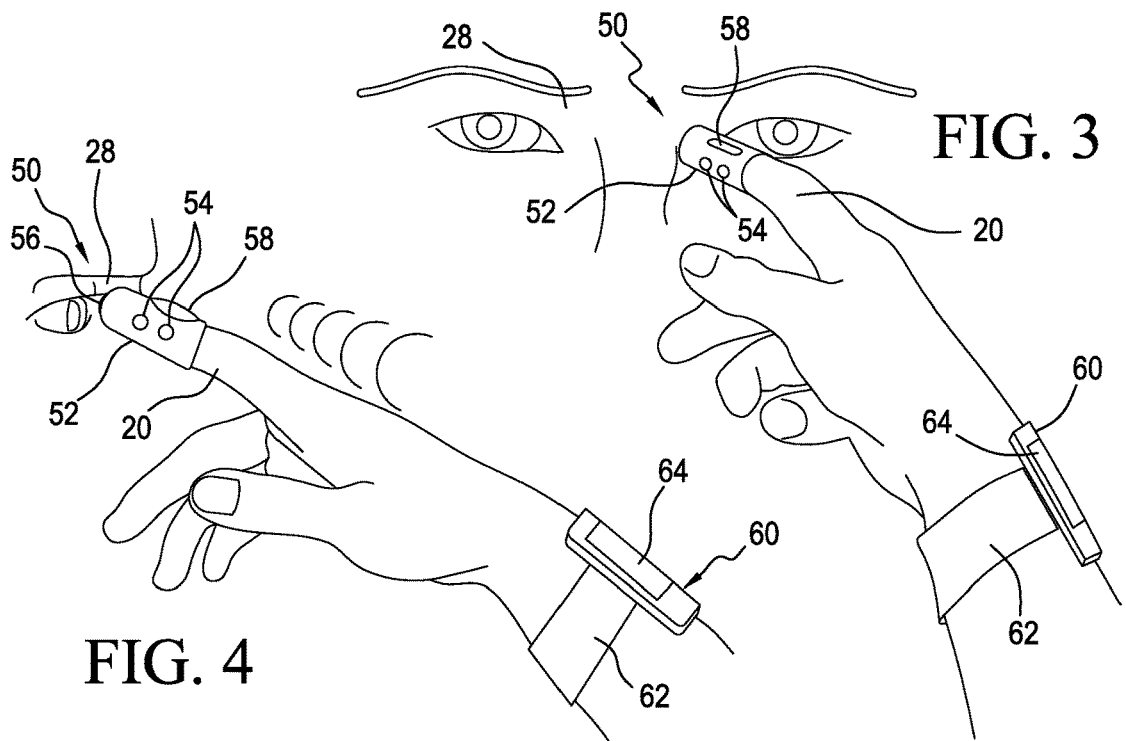
FIG. 3
FIG. 4
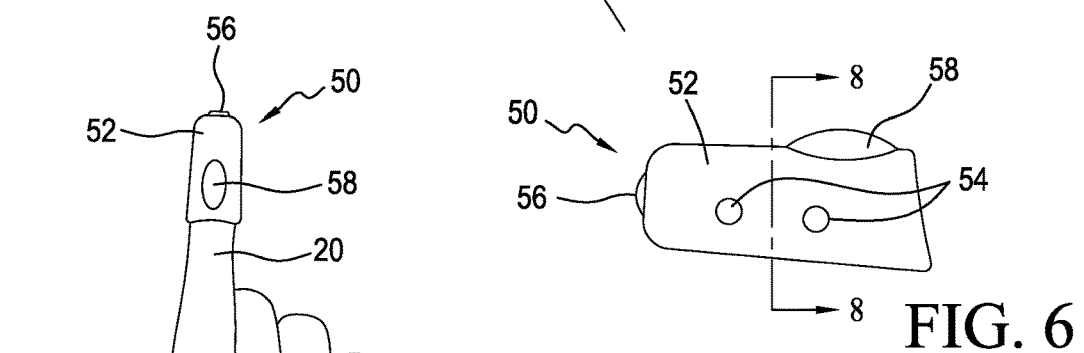
FIG. 5
FIG. 6
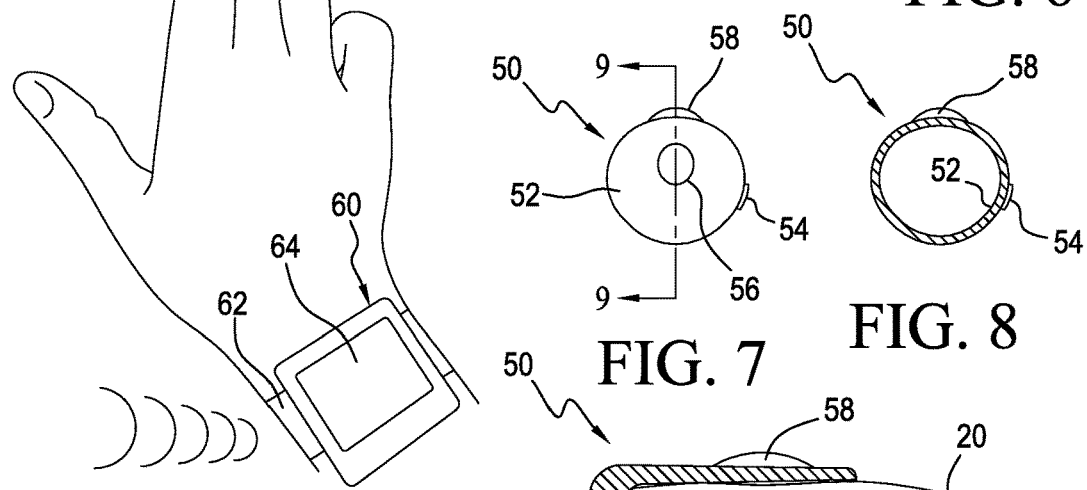
FIG. 7
FIG. 8
FIG. 9

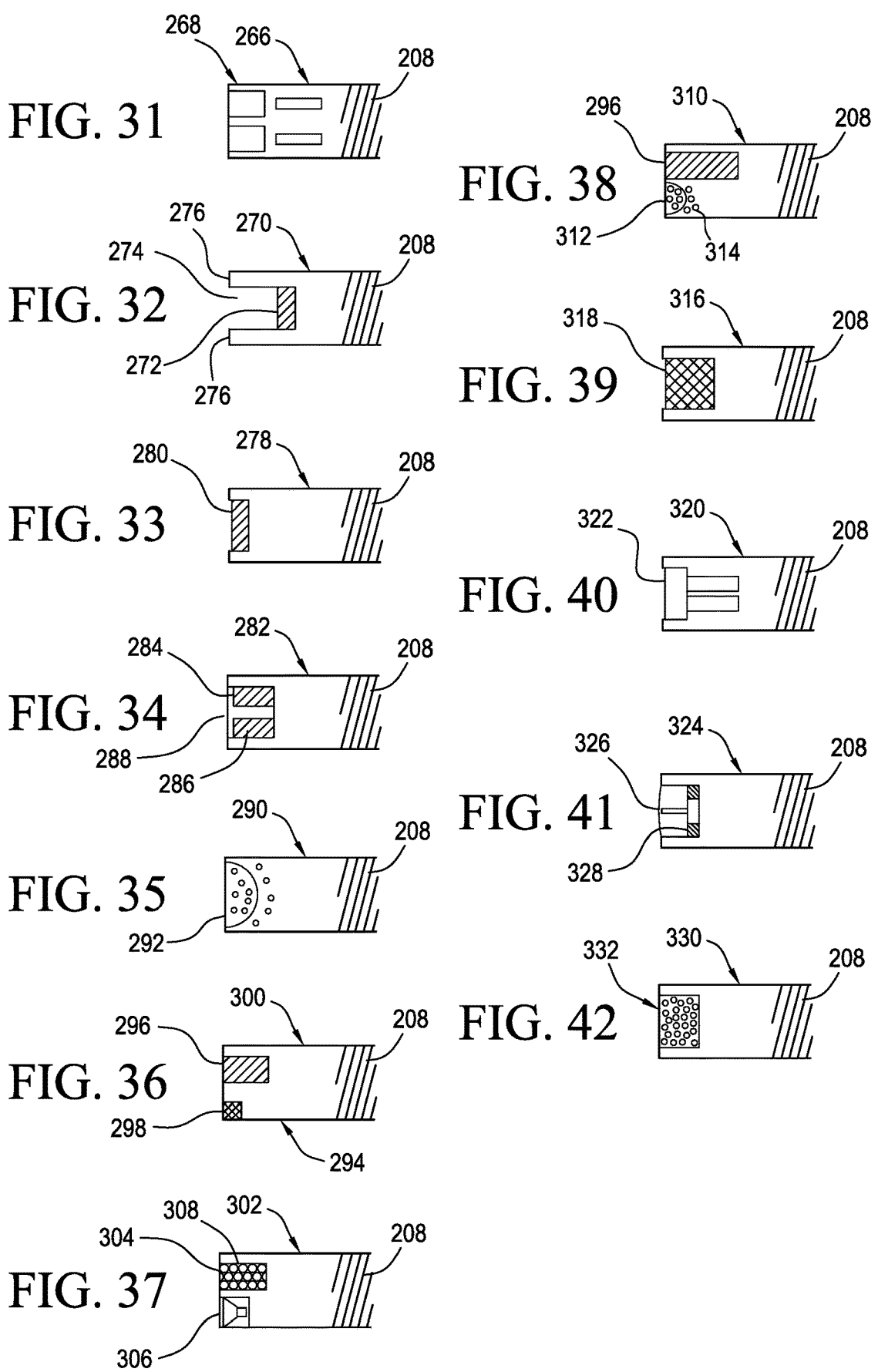

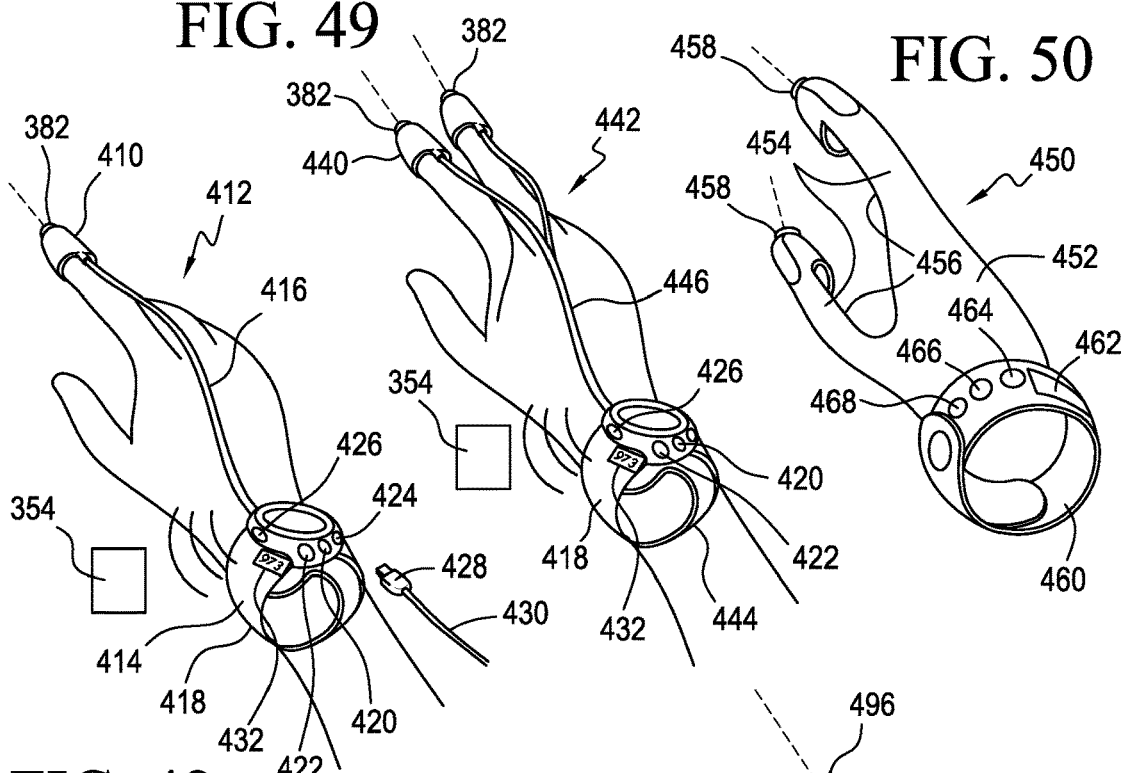
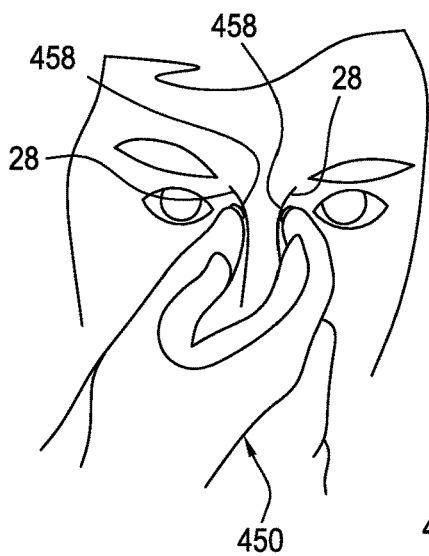
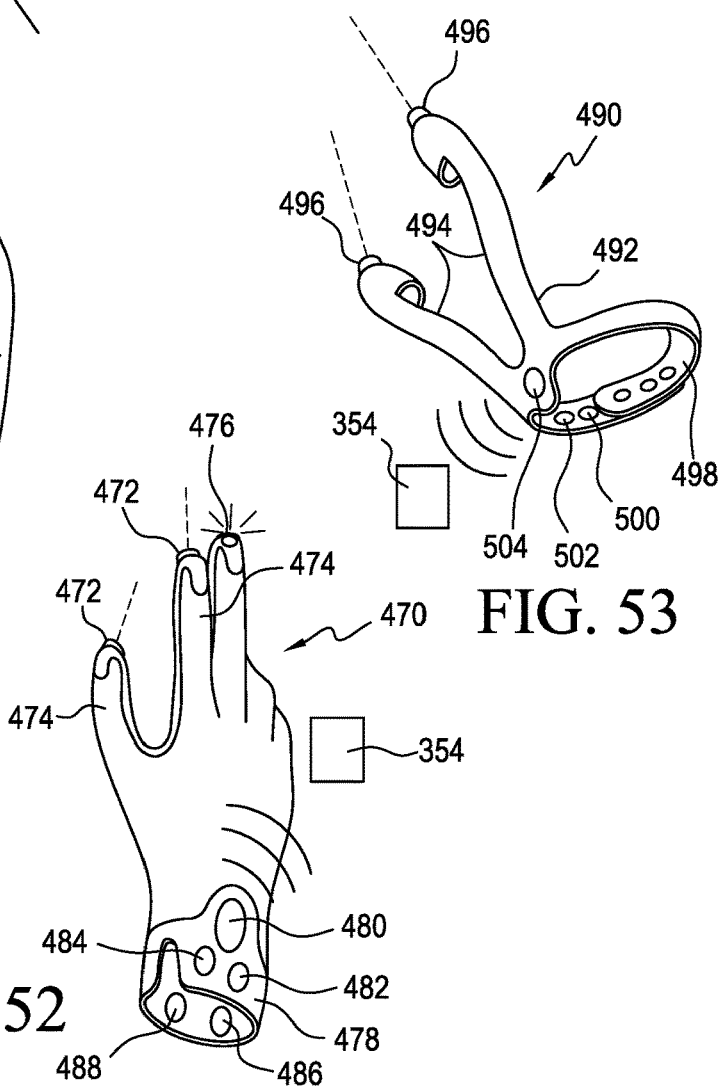
FIG. 49
FIG. 50
FIG. 48
FIG. 51
FIG. 53
FIG. 52

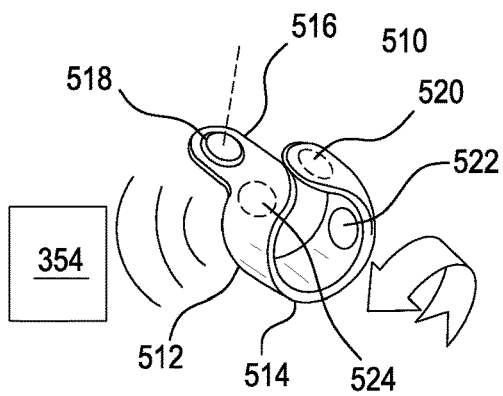
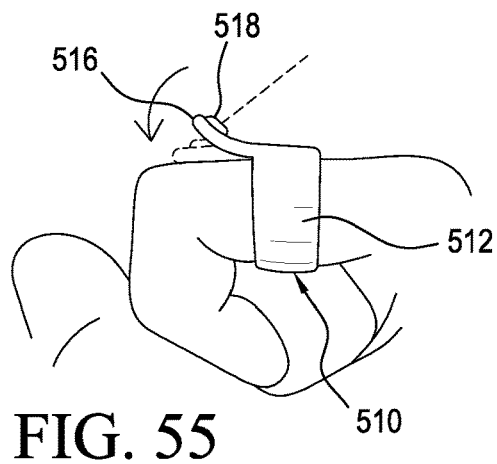
FIG. 54
FIG. 55
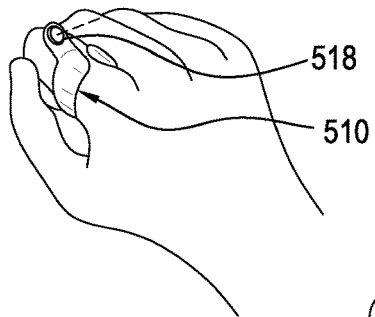
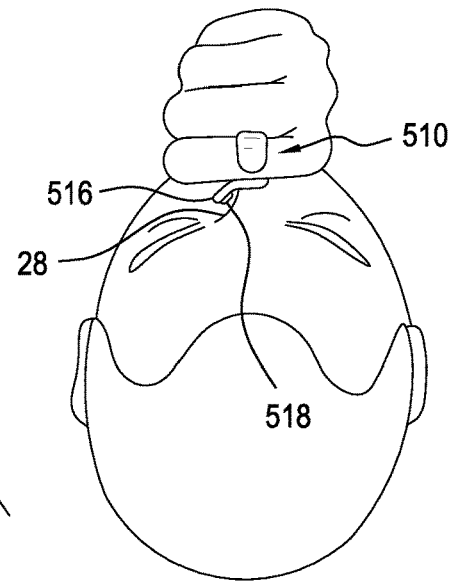
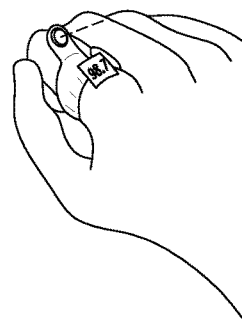
FIG. 56
FIG. 58
FIG. 57
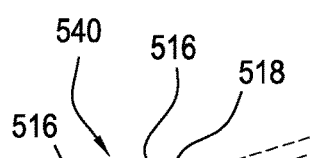
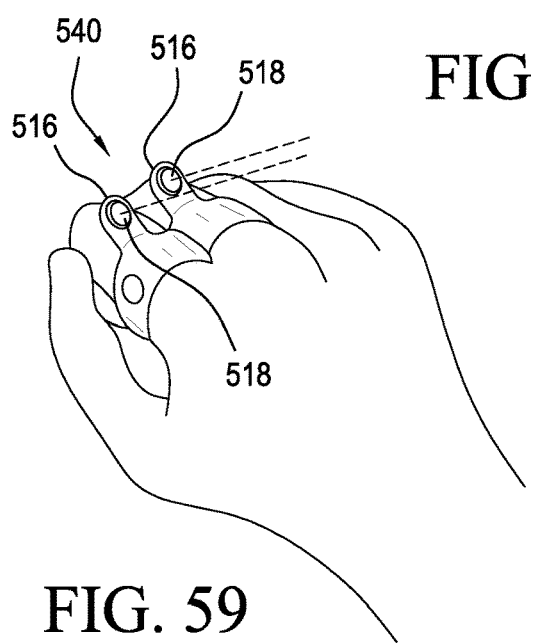
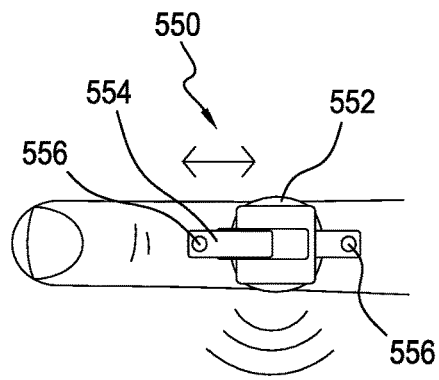
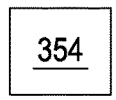
FIG. 59
FIG. 60

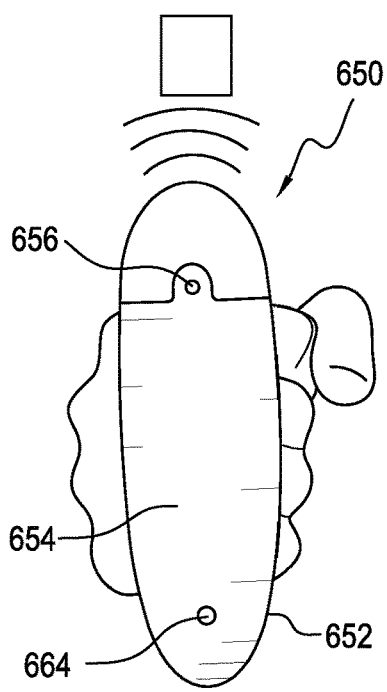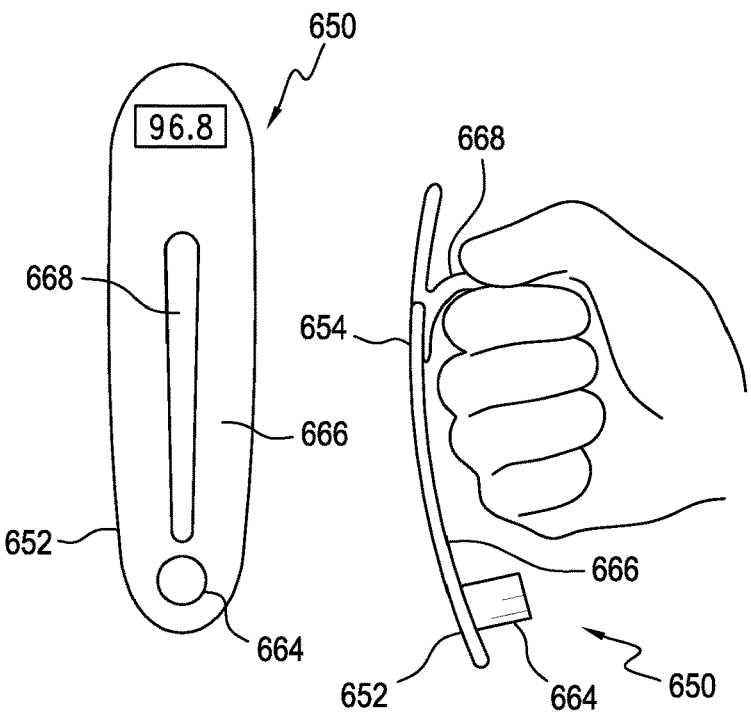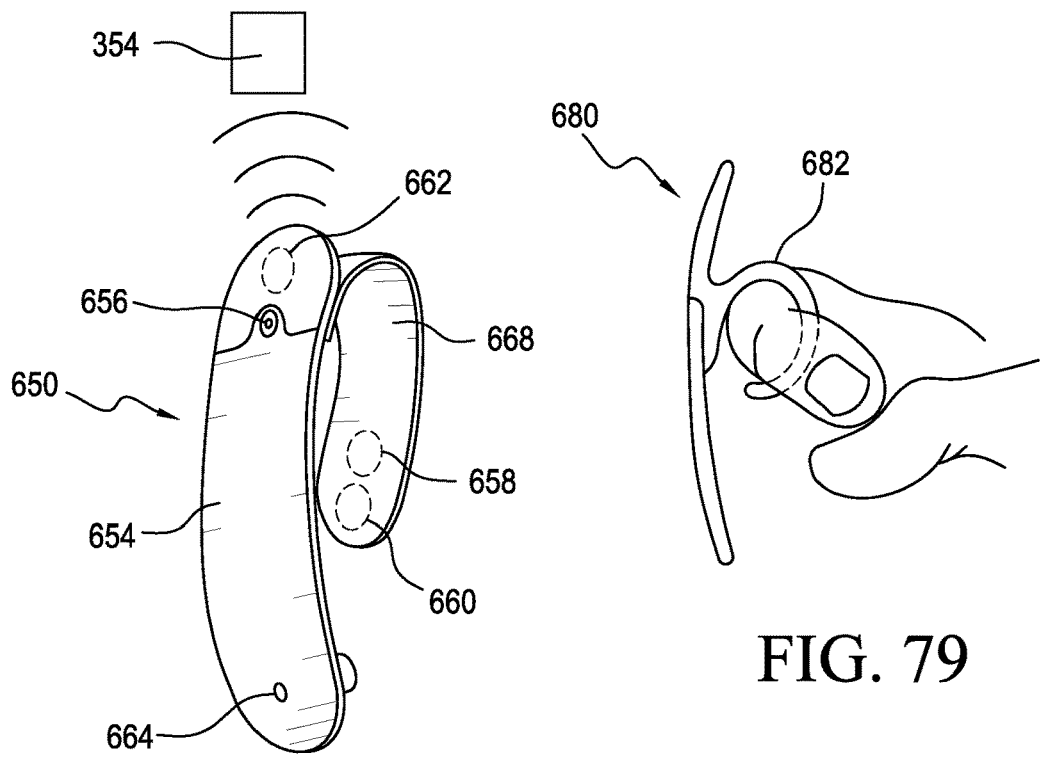
FIG. 75
FIG. 76
FIG. 77
FIG. 78
FIG. 79

WEARABLE DEVICES CONFIGURED TO SUPPORT MEASUREMENT AND TRANSMISSION APPARATUS

CROSS-REFERENCE TO RELATED APPLICATIONS

This application claims the benefit of priority to U.S. Provisional Patent Application No. 62/140,989, filed on Mar. 31, 2015, which is hereby incorporated by reference in its entirety.

TECHNICAL FIELD

This disclosure relates to wearable devices configured to support a measurement and/or a transmission apparatus.

BACKGROUND

Measurement and transmission devices, particularly those associated with medical functions, are typically large and expensive devices. Furthermore, such devices can be difficult to position for proper measurement and/or therapeutic transmission.

SUMMARY

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 3 shows a view of a further wearable device in accordance with an exemplary embodiment of the present disclosure.

FIG. 4 shows another view of the wearable device of FIG. 3.

FIG. 5 shows yet another view of the wearable device of FIG. 3.

FIG. 6 shows a side view of the wearable device of FIG. 3.

FIG. 7 shows an end view of the wearable device of FIG. 3.

FIG. 8 shows a cross-sectional view of the device of FIG. 6 along the lines 8-8.

FIG. 9 shows a cross-sectional view of the device of FIG. 7 along the lines 9-9.

FIG. 31 shows a schematic view of a sixteenth device configured to be positioned on a wearable device in accordance with an exemplary embodiment of the present disclosure.

FIG. 32 shows a schematic view of a seventeenth device configured to be positioned on a wearable device in accordance with an exemplary embodiment of the present disclosure.

FIG. 33 shows a schematic view of an eighteenth device configured to be positioned on a wearable device in accordance with an exemplary embodiment of the present disclosure.

FIG. 34 shows a schematic view of a nineteenth device configured to be positioned on a wearable device in accordance with an exemplary embodiment of the present disclosure.

FIG. 35 shows a schematic view of a twentieth device configured to be positioned on a wearable device in accordance with an exemplary embodiment of the present disclosure.

FIG. 36 shows a schematic view of a twenty-first device configured to be positioned on a wearable device in accordance with an exemplary embodiment of the present disclosure.

FIG. 37 shows a schematic view of a twenty-second device configured to be positioned on a wearable device in accordance with an exemplary embodiment of the present disclosure.

FIG. 38 shows a schematic view of a twenty-third device configured to be positioned on a wearable device in accordance with an exemplary embodiment of the present disclosure.

FIG. 39 shows a schematic view of a twenty-fourth device configured to be positioned on a wearable device in accordance with an exemplary embodiment of the present disclosure.

FIG. 40 shows a schematic view of a twenty-fifth device configured to be positioned on a wearable device in accordance with an exemplary embodiment of the present disclosure.

FIG. 41 shows a schematic view of a twenty-sixth device configured to be positioned on a wearable device in accordance with an exemplary embodiment of the present disclosure.

FIG. 42 shows a schematic view of a twenty-seventh device configured to be positioned on a wearable device in accordance with an exemplary embodiment of the present disclosure.

FIG. 48 shows a view of yet an even further thimble-like device in accordance with an exemplary embodiment of the present disclosure.

FIG. 49 shows a view of still another thimble-like device in accordance with an exemplary embodiment of the present disclosure.

FIG. 50 shows a view of a glove device in accordance with an exemplary embodiment of the present disclosure.

FIG. 51 shows a view of the glove device of FIG. 50 in use by a patient or subject.

FIG. 52 shows a view of another glove device in accordance with an exemplary embodiment of the present disclosure.

FIG. 53 shows a view of a further glove device in accordance with an exemplary embodiment of the present disclosure.

FIG. 54 shows a view of a ring or ring-like device in accordance with an exemplary embodiment of the present disclosure.

FIG. 55 shows a view of the ring or ring-like device of FIG. 54 being worn by a user.

FIG. 56 shows another view of the ring or ring-like device of FIG. 54 being worn by the user.

FIG. 57 shows a further view of the ring or ring-like device of FIG. 54 being operated by the user.

FIG. 58 shows a view of another ring or ring-like device in accordance with an exemplary embodiment of the present disclosure.

FIG. 59 shows a view of yet another ring or ring-like device in accordance with an exemplary embodiment of the present disclosure.

FIG. 60 shows a view of an even further ring or ring-like device in accordance with an exemplary embodiment of the present disclosure.

FIG. 75 shows a view of a hand supported device in accordance with an exemplary embodiment of the present disclosure.

FIG. 76 shows a back view of the device of FIG. 75.

FIG. 77 shows a side view of the device of FIG. 75.

FIG. 78 shows a perspective view of the device of FIG. 75.

FIG. 79 shows a view of another device in accordance with an exemplary embodiment of the present disclosure.

DETAILED DESCRIPTION

Devices to measure parameters and to output or transmit signals, medicine, heat, etc., are well known. It is typical for these devices to be expensive and relatively large, with each of these devices being specialized for a specific function. For example, specialized devices exist to test blood glucose. The present disclosure describes devices that take a different approach to parameter measurement and output or transmission of signals, medicine, heat, etc. These devices are compact, versatile, relatively inexpensive, and require minimal training to be effectively used.

Figure 1:
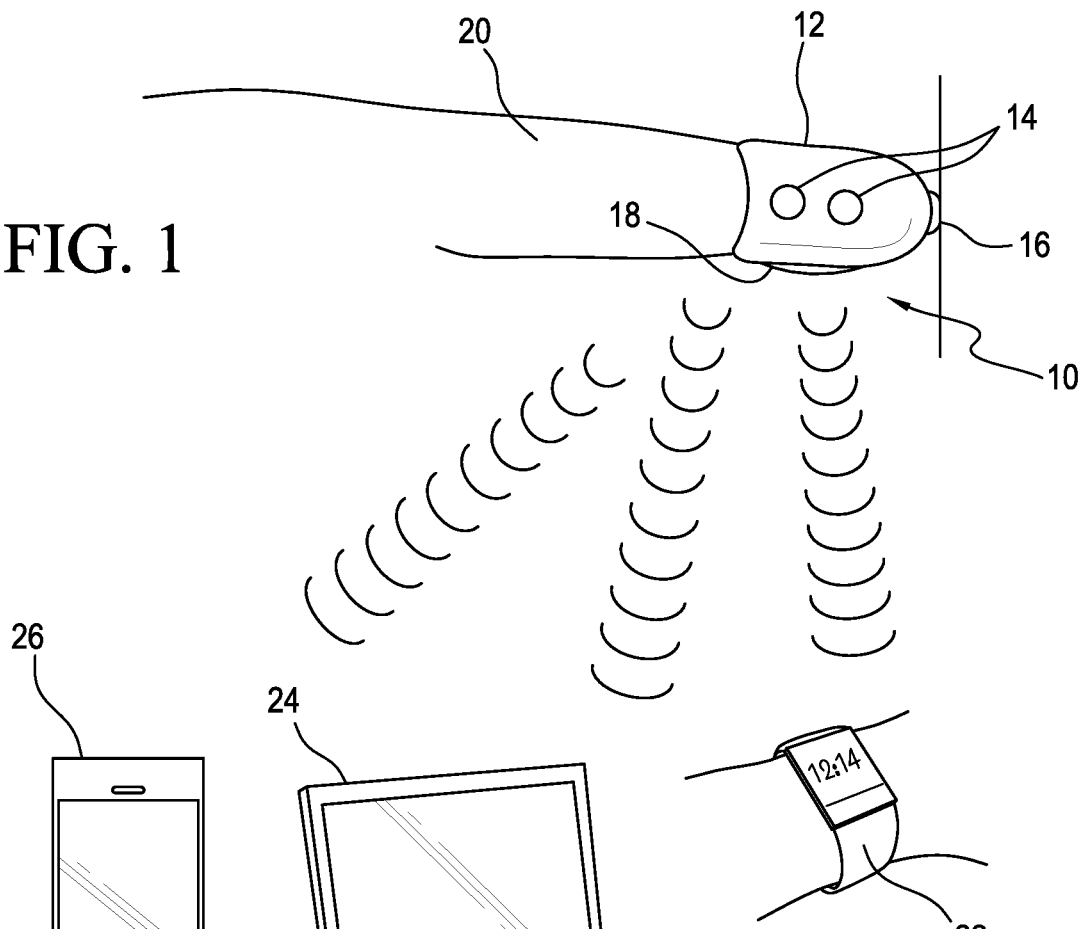
FIG. 1 shows a view of a wearable device in accordance with an exemplary embodiment of the present disclosure.

FIG. 1 shows a wearable device in accordance with an exemplary embodiment of the present disclosure, indicated generally at 10. Wearable device 10 is configured to include a device body 12, a power supply 14, a contact element 16, and a transmitter, receiver, or transceiver 18. Device body 12 is configured to be positioned on and entirely supported by a finger 20 of a user. Because of the location of device body 12 on finger 20, device 10 can be described as a thimble sensor, thimble transmitter, thimble delivery device, etc., depending on the type of contact element 16 positioned on device body 12. Power supply 14 is configured to provide electrical power for electrical elements of device 10. Contact element 16 can be configured to include any one of a plurality of contact sensing, measurement, or output devices described in more detail herein. It should be understood that in the exemplary embodiments disclosed, the output devices described herein are configured to provide an output to skin, which can be human skin. In an exemplary embodiment, contact element 16 is a plug-in device; i.e., a user can remove one contact element 16 and replace it with another contact element 16, which provides device 10 with the capability of performing many different functions. If contact element 16 is a measurement or sensing device, signals from contact element 16 are transmitted by transmitter 18 to a separate electronic device 22, 24, and/or 26, which is configured to receive the transmitted signals to analyze, display, and/or store the signals. Separate electronic device 22, 24, and/or 26 can be, for example, a watch, laptop, tablet, cell phone, computer, or other similar device. It should be understood that contact element 16 can be replaced by a temperature modification device such as a Peltier device, resistive device, and other thermal devices or light emitting device, including devices described in co-pending U.S. patent application Ser. No. 15/067,030 filed on Mar. 10, 2016, which claims priority to provisional Pat. Appl. No. 62/131,056 filed on Mar. 10, 2015, Applicant, the entire contents of which are hereby incorporated by reference in their entirety. U.S. patent application Ser. No. 15/067,030 describes an ABTT terminus as being located between an eye and the eyebrow to measure parameters of a brain core of a human body. The ABTT terminus is described as being located at a convergence of a facial vein, a supraorbital vein and a frontal vein of the upper eyelid adjacent to the bridge of the nose.

Figure 2:
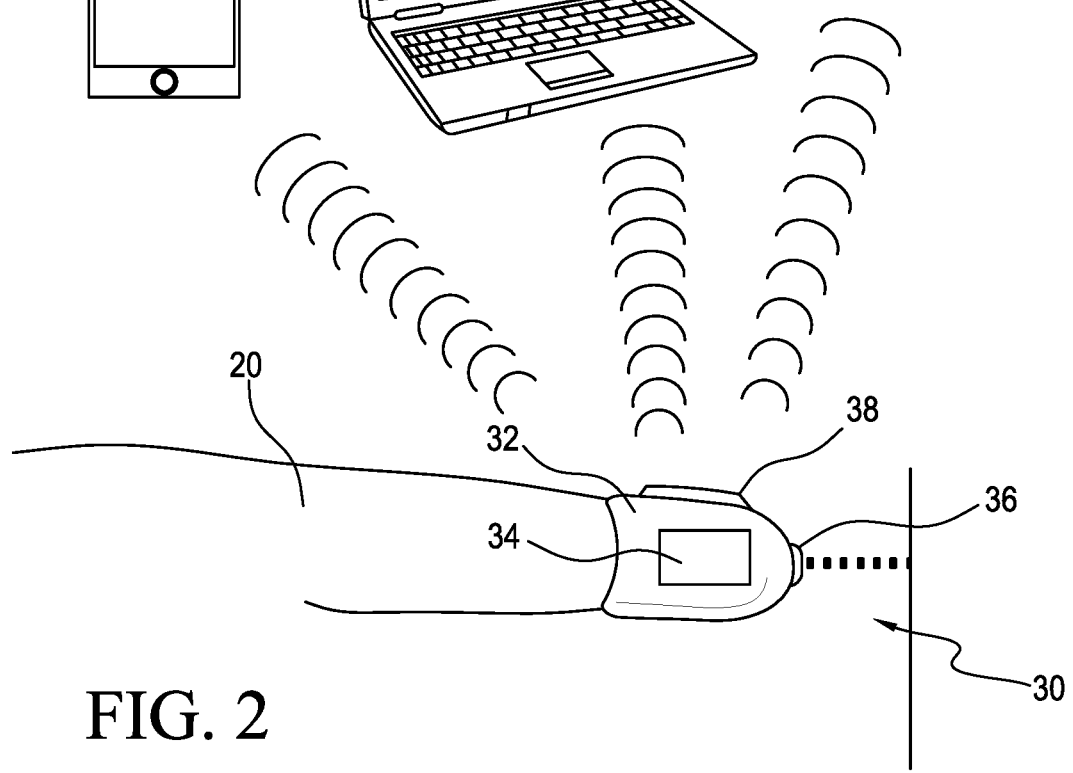
FIG. 2 shows a view of a wearable device in accordance with another exemplary embodiment of the present disclosure.

FIG. 2 shows a wearable device in accordance with another exemplary embodiment of the present disclosure, indicated generally at 30. Wearable device 30 is configured to include a device body 32, a power supply 34, an element 36, and a transmitter, receiver, or transceiver 38. Device body 32 is configured to be positioned on finger 20 of a user. Because of the location of device body 32 on finger 20, device 30 can be described as a thimble sensor, thimble transmitter, thimble delivery device, etc., depending on the type of element 36 positioned on device body 32. Power supply 34 is configured to provide electrical power for electrical elements of device 30. Element 36 can be configured to include any one of a plurality of non-contact sensing, measurement, or output devices described in more detail herein. In an exemplary embodiment, element 36 is a plug-in device; i.e., a user can remove one element 36 and replace it with another element 36, which provides device 30 with the capability of performing many different functions. If element 36 is a measurement or sensing device, signals from element 36 are transmitted by transmitter 38 to separate electronic device 22, 24, and/or 26, which is configured to receive the transmitted signals to analyze, display, and/or store the signals. Separate electronic device 22, 24, and/or 26 can be, for example, a watch, laptop, tablet, cell phone, FIGS. 3-9 show a further wearable device in accordance with an exemplary embodiment of the present disclosure, indicated generally at 50. Wearable device 50 is configured to include a device body 52, a power supply 54, a contact element in the form of a thermal scanner 56, and a transmitter, receiver, or transceiver 58. Device body 52 is configured to be positioned on finger 20 of a user. Because of the location of device body 52 on finger 20, device 50 can be described as a thimble sensor. Power supply 54 is configured to provide electrical power for electrical elements of device 50. Thermal scanner 56 is configured to acquire temperature readings of an Abreu brain thermal tunnel (ABTT) terminus 28. Signals from thermal scanner 56 are transmitted by transmitter 38 to a separate electronic device 60, which is configured to receive the transmitted signals to analyze, display, and/or store the signals. Separate electronic device 60 is shown as a wrist-mounted device, which can also function as a watch. In the exemplary embodiment of FIGS. 3-5, device 50 is configured to include a wrist support or strap 62 and a display 64.

A user can guide thermal scanner 56 by analysis of the signals transmitted from device 50 to separate electronic device 60. Because the temperature of ABTT terminus 28 is typically higher than the temperature of surrounding skin, separate electronic device 60 is configured to determine a peak temperature, and to guide thermal scanner 56 to the location of the peak temperature. Such guidance can be by notification presented on display 64, by flashing of display 64 or other visual indicator, or an audio output (not shown).

Though device 50 is configured to include thermal scanner 56, it should be understood that device 50 can be configured to include other elements, similar to devices 10 and 30. It should be understood that thermal scanner 56 can include an infrared detector coupled to a light emitter.

Figure 10:
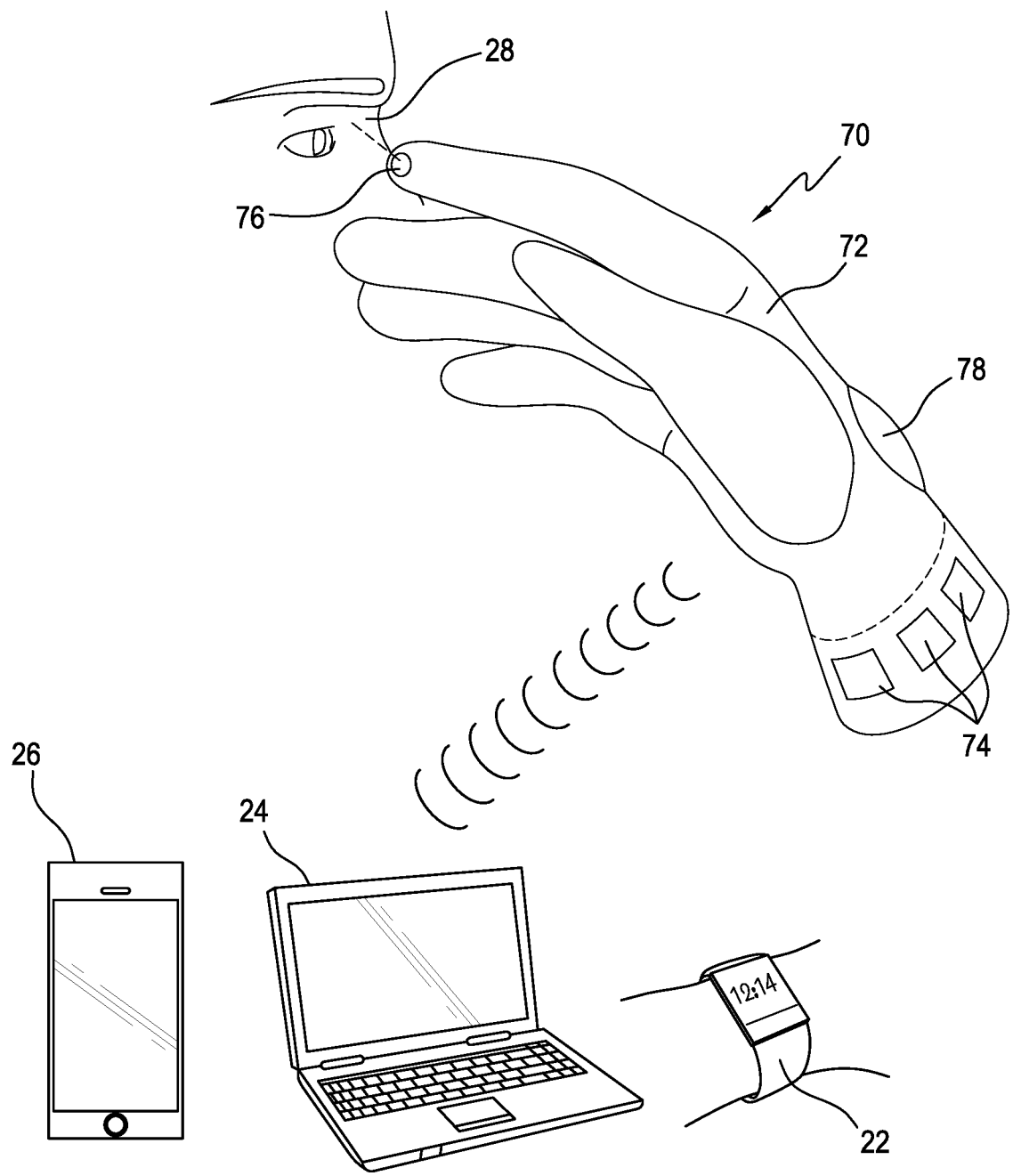
FIG. 10 shows a view of yet another wearable device in accordance with an exemplary embodiment of the present disclosure.
Figure 11:
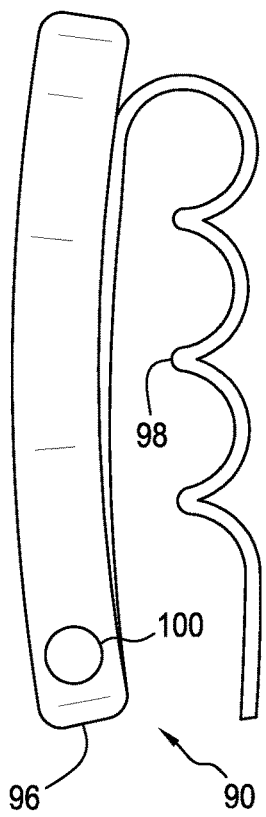
FIG. 11 shows a view of a device in accordance with an exemplary embodiment of the present disclosure.
Figure 12:
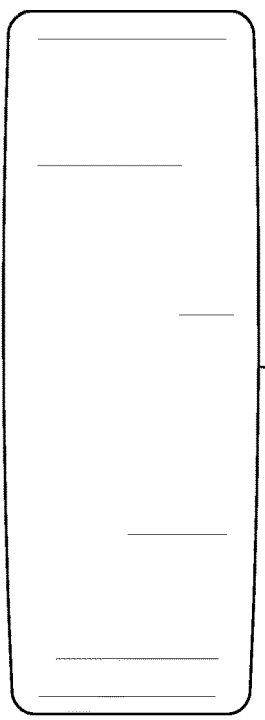
FIG. 12 shows a front view of the device of FIG. 11.
Figure 13:
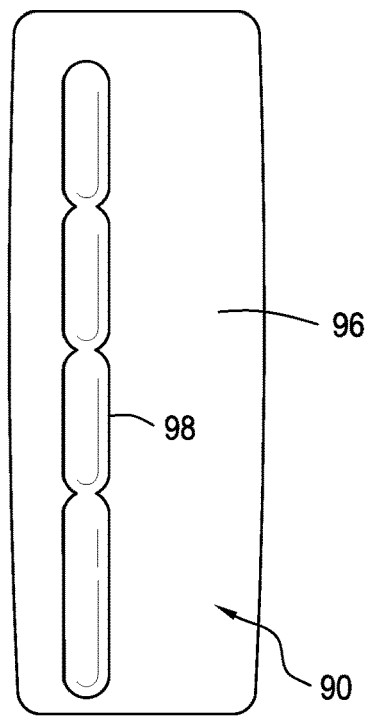
FIG. 13 shows a back view of the device of FIG. 11.
Figure 14:
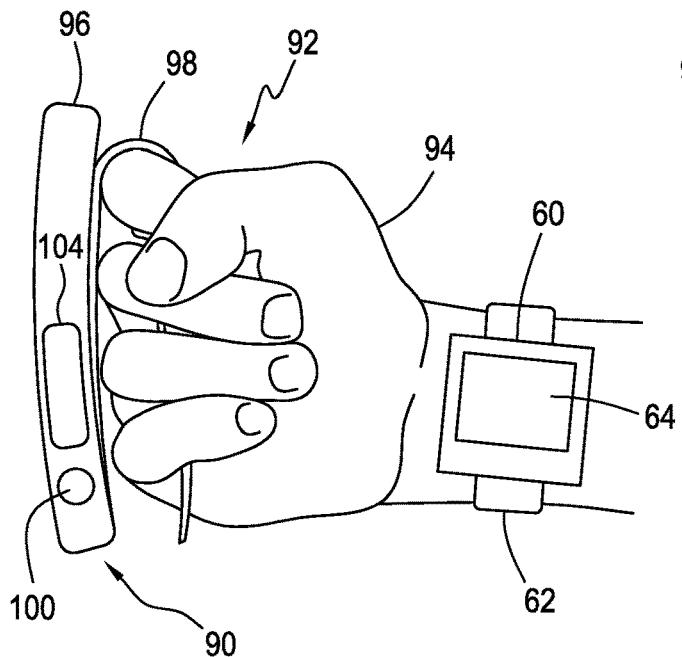
FIG. 14 shows a view of the device of FIG. 11 positioned on a user's hand.
Figure 15:
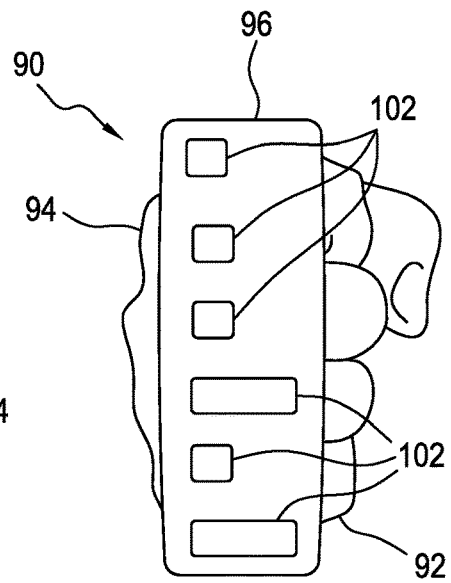
FIG. 15 shows a front view of the device of FIG. 11 positioned on a user's hand.

FIG. 10 shows a view of yet another wearable device in accordance with an exemplary embodiment of the present disclosure, indicated generally at 70. Wearable device 70, which is configured as a glove, is configured to include a device body 72, a power supply 74, a contact element in the form of a thermal sensor 76, and a transmitter, receiver, or transceiver 78. Device body 72 is configured to be positioned on a hand (not shown) of a user. Power supply 74 is configured to provide electrical power for electrical elements of device 70. Thermal sensor 76 is configured to acquire temperature readings of ABTT terminus 28. Signals from thermal sensor 76 are transmitted by transmitter 78 to separate electronic device 22, 24, and/or 26, which is configured to receive the transmitted signals to analyze, display, and/or store the signals.

Though device 70 is configured to include thermal sensor 76, it should be understood that device 70 can be configured to include other contact or non-contact elements, similar to devices 10 and 30. Furthermore, though device 70 shows a sensor on an index finger, it should be understood that device 70 can be configured with sensor or output elements on other fingers, including a thumb.

FIGS. 11-15 are views of a holdable or wearable device in accordance with an exemplary embodiment of the present disclosure, indicated generally at 90. Device 90, which is configured to be held by fingers 92 of hand 94 in a manner similar to brass knuckles, is configured to include a device body 96, a finger or hand grip 98, a power supply 100, a plurality of input or sensor and output or delivery elements 102, and a transmitter, receiver, or transceiver 104. Finger or hand grip 98 is configured to be attached or positioned on device body 96. Device body 96 is configured to support power supply 100, elements 102, and transmitter 104. Power supply 100 is configured to provide electrical power for electrical elements of device 90. Signals from elements 102 are transmitted by transmitter 104 to separate electronic device 22, 24, 26, or 60, which are configured to receive the transmitted signals to analyze, display, and/or store the signals.

The plurality of elements 102 permits device 90 to move from one measurement to another rapidly, permits multiple, simultaneous measurements, permits one or more outputs, or a combination of inputs or measurements and outputs or deliveries, depending on the types of inputs and outputs and the location where the inputs and outputs are positioned. For example, a blood glucose measurement could be taken while medication is delivered. In another example, temperature, pulse rate, and glucose levels could be measured while a medication and/or optical therapy is delivered. It should be understood that elements 102 can be configured as contact or non-contact devices, including a mixture of both.

FIGS. 16-42 show schematic representations of various types of devices that can be elements 16, 36, 56, 76, and 102, in accordance with exemplary embodiments of the present disclosure.

Figure 16:
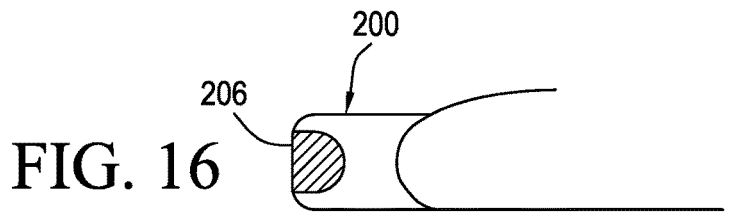
FIG. 16 shows a schematic view of a first device configured to be positioned on a wearable device in accordance with an exemplary embodiment of the present disclosure.

FIG. 16 shows a schematic view of a contact input or output element 200, which is configured to include an input or output contact device 202. Sensor element 202 can be many different elements, such as a temperature sensor.

Figure 17:
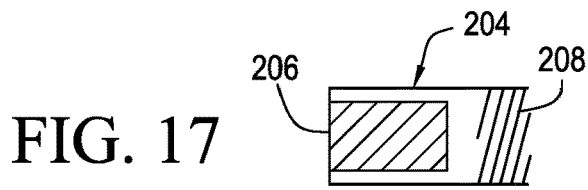
FIG. 17 shows a schematic view of a second device configured to be positioned on a wearable device in accordance with an exemplary embodiment of the present disclosure.

FIG. 17 shows a schematic view of an output element 204, which is configured to include an ultrasonic output device 206. Output element 204 is configured to include a fastening arrangement 208 that is configured to attach output element 204 to one of the wearable devices described herein. Fastening arrangement 208 can be configured as screw threads, a bayonet mount, or other types of mounting arrangements.

Figure 18:
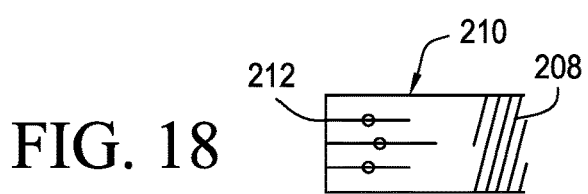
FIG. 18 shows a schematic view of a third device configured to be positioned on a wearable device in accordance with an exemplary embodiment of the present disclosure.

FIG. 18 shows a schematic view of a contact element 210, which is configured to include an electronic contact device 212.

Figure 19:
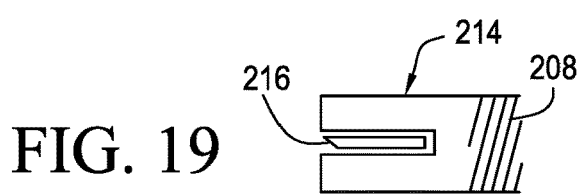
FIG. 19 shows a schematic view of a fourth device configured to be positioned on a wearable device in accordance with an exemplary embodiment of the present disclosure.

FIG. 19 shows a schematic view of a contact element 214, which is configured to include a needle 216. Needle 216 can be configured to deliver a medication, a drug, or another chemical. Needle 216 can be configured to be extended from contact element 214 by a predetermined amount, can be extended by the action of a finger, or can be extended by a mechanical apparatus, which can be manually or electrically operated.

Figure 20:
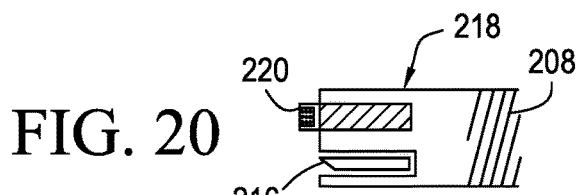
FIG. 20 shows a schematic view of a fifth device configured to be positioned on a wearable device in accordance with an exemplary embodiment of the present disclosure.

FIG. 20 shows a schematic view of a contact element 218, which is configured to include needle 216, which can be configured as described herein, and a glucose meter strip 220, said needle 216 and said glucose meter strip 220 are disposed next to each other, and adapted for blood drawn after puncturing the skin by the needle 216 to be carried towards glucose meter strip 220.

Figure 21:
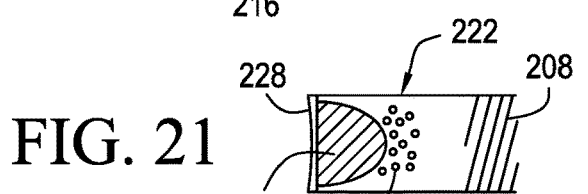
FIG. 21 shows a schematic view of a sixth device configured to be positioned on a wearable device in accordance with an exemplary embodiment of the present disclosure.

FIG. 21 shows a schematic view of a contact element 222, which is configured to include an absorbent material 224 that is configured to include a drug, medication, or chemical 226. Absorbent material 224 can be covered by a removable or peelable layer 228, which is removed prior to application of contact element 222 to the skin of a subject or patient.

Figure 22:
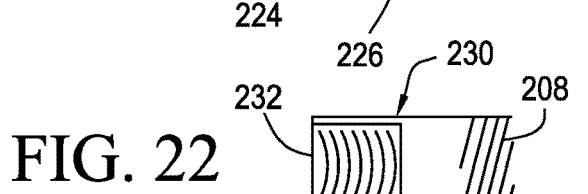
FIG. 22 shows a schematic view of a seventh device configured to be positioned on a wearable device in accordance with an exemplary embodiment of the present disclosure.

FIG. 22 shows a schematic view of an element 230, which is configured to include a magnetic sensor 232.

Figure 23:
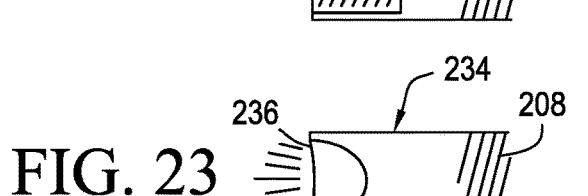
FIG. 23 shows a schematic view of an eighth device configured to be positioned on a wearable device in accordance with an exemplary embodiment of the present disclosure.

FIG. 23 shows a schematic view of an output element 234, which is configured to include a fluorescent light 236.

Figure 24:
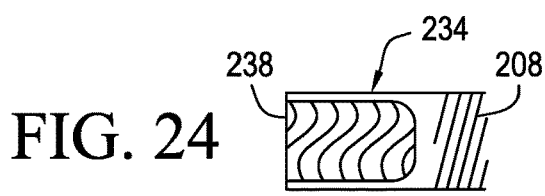
FIG. 24 shows a schematic view of a ninth device configured to be positioned on a wearable device in accordance with an exemplary embodiment of the present disclosure.

FIG. 24 shows a schematic view of an output element 238, which is configured to include a microwave emitter 240.

Figure 25:
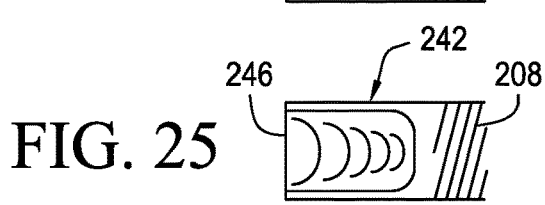
FIG. 25 shows a schematic view of a tenth device configured to be positioned on a wearable device in accordance with an exemplary embodiment of the present disclosure.

FIG. 25 shows a schematic view of an output element 242, which is configured to include a radio frequency (RF) emitter 244.

Figure 26:
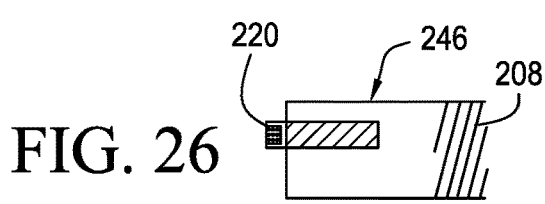
FIG. 26 shows a schematic view of an eleventh device configured to be positioned on a wearable device in accordance with an exemplary embodiment of the present disclosure.

FIG. 26 shows a schematic view of a contact element 246, which is configured to include glucose meter strip 248.

Figure 27:
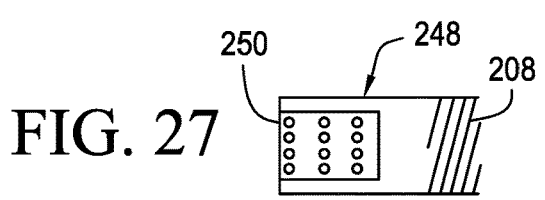
FIG. 27 shows a schematic view of a twelfth device configured to be positioned on a wearable device in accordance with an exemplary embodiment of the present disclosure.

FIG. 27 shows a schematic view of a contact element 248, which is configured to include a sample collector, including a surface having pores and one-way valves for acquiring a sample such as a body secretion, blood, or any type of material biologic or non-biologic (such as powder, dust, rocks, and the like) for analysis in-situ or for storage, said collector including a reservoir.

Figure 28:
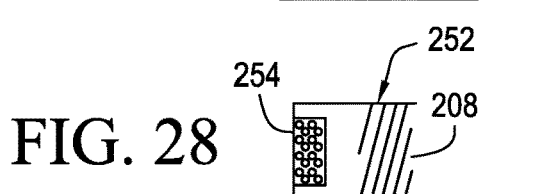
FIG. 28 shows a schematic view of a thirteenth device configured to be positioned on a wearable device in accordance with an exemplary embodiment of the present disclosure.

FIG. 28 shows a schematic view of an input element 252, which is configured to include a sound receiving device 254, such as a microphone. However, it should be understood that other devices, such as piezoelectric devices, can be sensitive to sound vibrations while not necessarily serving as a microphone. Such devices may allow a physician to listen to heart sounds by wearing the specialized gloves and thimbles of the present disclosure. As the doctor touches the heart area with his/her fingers, heart sounds are captured by the microphone and transmitted to a processor that analyzes the sounds, and if an abnormal heart sound or murmur is detected, an alert system is activated and reports the abnormality by any of the visual and/or audio systems described in the present disclosure, including but not limited to, local reporting on the glove or thimble device, or wirelessly by a remote device including watch, cell phone, tablet, computer, glasses, and any other electronic device. It should be understood that any electronic device described in the present disclosure such a watch can be connected by wire to the thimble=like or glove-like devices of the invention.

Figure 29:
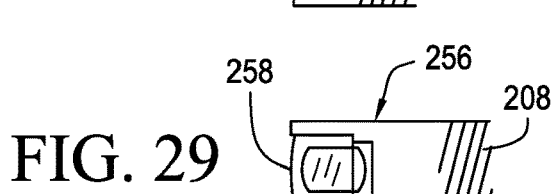
FIG. 29 shows a schematic view of a fourteenth device configured to be positioned on a wearable device in accordance with an exemplary embodiment of the present disclosure.

FIG. 29 shows a schematic view of an input element 256, which is configured to include a camera 258. A glove-like device of the present disclosure allows a surgeon while operating on a patient and while holding internal organs to take photo of such internal organs.

Figure 30:
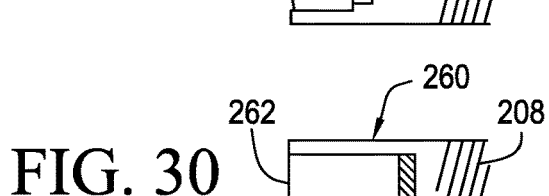
FIG. 30 shows a schematic view of a fifteenth device configured to be positioned on a wearable device in accordance with an exemplary embodiment of the present disclosure.

FIG. 30 shows a schematic view of an input element 260, which is configured to include a lens assembly 262, which can be configured to include a filter, and a detector 264, which can be configured as a light detector or an array.

FIG. 31 shows a schematic view of a contact element 266, which is configured to include a plurality of emitter and detector devices 268. Emitter and detector devices 268 can be one or more of the input and output devices described herein. Such devices can be operated in an offset fashion with respect to time to permit emission and subsequent detection with blooming or overwhelming the detector. Such complementary devices can be, for example, a heating device and a temperature measurement device, or alternatively as a light emitter-detector pair, FIG. 32 shows a schematic view of a contact element 270, which is configured to include a non-contact sensor 272. Non-contact sensor 272 is configured to be positioned in a recess 274 of contact element 270 while an end 276 of contact element 270 abuts the skin of a subject or patient.

FIG. 33 shows schematic view of a non-contact element 278, which is configured to include a non-contact sensor 280.

FIG. 34 shows a schematic view of a non-contact element 282, which is configured to include an emitter 284 and a detector 286, which are positioned in a recess 288 of non-contact element 282. It should be understood that emitter-detector pair can also be located on the surface, and touch the skin during measurement as for example a pulse oximeter.

FIG. 35 shows a schematic view of a contact element 290, which is configured to include an iontophoresis drug, medication, or chemical delivery system 292.

FIG. 36 shows a schematic view of a contact element 294, which is configured to include a heating and/or cooling device 296, and a temperature sensor 298. Contact element 294 is further configured to include an element body 300, which is configured to be thermally insulating to minimize transmission of heat between device 296 and temperature sensor 298.

FIG. 37 shows a schematic view of an input/output element 302, which is configured to include a microphone or sound receiver 304 and a speaker or sound output 306. Input/output element 302 can be configured to include an element body 308, which can be configured to dampen vibrations emitted by sound output 306. Furthermore, sound receiver 304 can be configured to be positioned in a recess 308 of element body 308 to minimize picking up sound emitted by sound output 306 into air surrounding input/output element 302.

FIG. 38 shows a schematic view of a contact element 310, which is configured to include heating and/or cooling device 296, an absorbent material 312, and a drug, medication, or chemical 314.

FIG. 39 shows a schematic view of a contact element 316, which is configured to include a combination heating and/or cooling and blood pressure measuring device 318.

FIG. 40 shows a schematic view of a contact element 320, which is configured to include a pressure sensor plate 322 adapted to sense pulsations of a blood vessel and measure blood pressure. It should be understood that contact element 320 can include a microphone to capture sound from blood vessels.

FIG. 41 shows a schematic view of an input/output element 324, which is configured to include a laser diode assembly 326 and a detector 328. Input/output element 324 is configured to perform a Doppler measurement of a flow of blood.

FIG. 42 shows a schematic view of a contact element 330, which is configured to include a pressure sensor 332.

Figure 43:
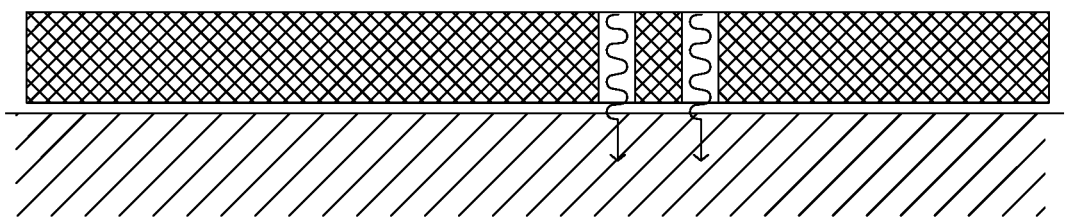
FIG. 43 shows a schematic view of a contact element for transmission of energy to the skin.

FIG. 43 illustrates an enlarged view of a contact element for transmission of energy to the skin.

Figure 44:
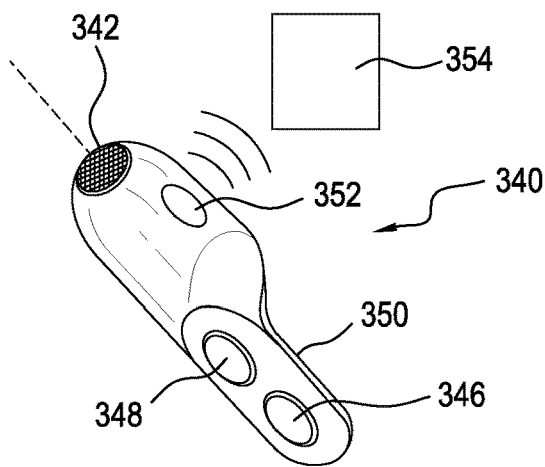
FIG. 44 shows a view of a thimble-like device in accordance with an exemplary embodiment of the present disclosure.

FIG. 44 shows a view of a thimble-like device, indicated generally at 340, in accordance with an exemplary embodiment of the present disclosure. Device 340 is configured to include a sensor 342, which in the embodiment of FIG. 44 is a thermometer. It should be understood that device 340 can include any medical device or other devices disclosed in the present disclosure and these wearable medical devices are within the scope of this embodiment. Device 340 is configured to include an essentially cylindrical device body 344. Device body 344 includes an extension, protrusion, or tongue 350 in which are positioned a power supply 346 and electronics 348. Sensor 342 can be similar to contact elements and non-contact elements described in previous embodiments. Device 340 also includes a transmitter, receiver, or transceiver 352 that is configured to communicate with a remote or separate electronic device 354, which can be, for example, a cell phone, watch, eyeglasses, tablet, computer, radios, and the like.

Figure 45:
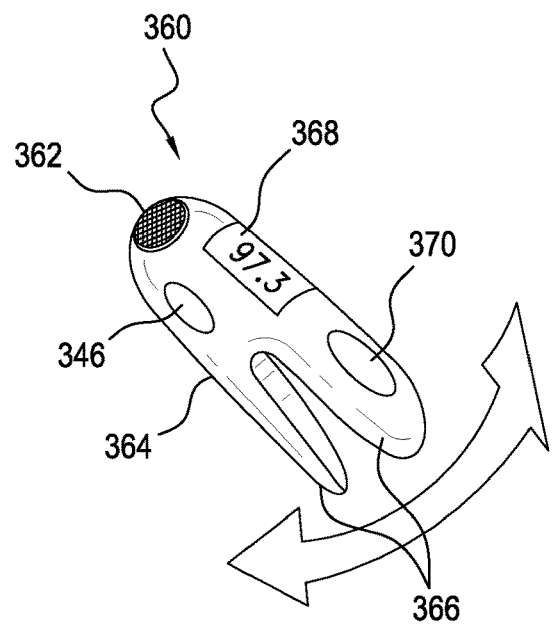
FIG. 45 shows a view of another thimble like device in accordance with an exemplary embodiment of the present disclosure.

FIG. 45 shows a view of another thimble like device, indicated generally at 360, in accordance with an exemplary embodiment of the present disclosure. Device 360 includes a sensor 362, a device body 364, and two extensions, protrusions, or tongues 366. Positioned on upper extension 366 is a display 368 and a speaker 370, each of which can be used for reporting of a measured value. As with device 340, device 360 includes power supply 346, and can include a transmitter, a processor, and other elements.

Figure 46:
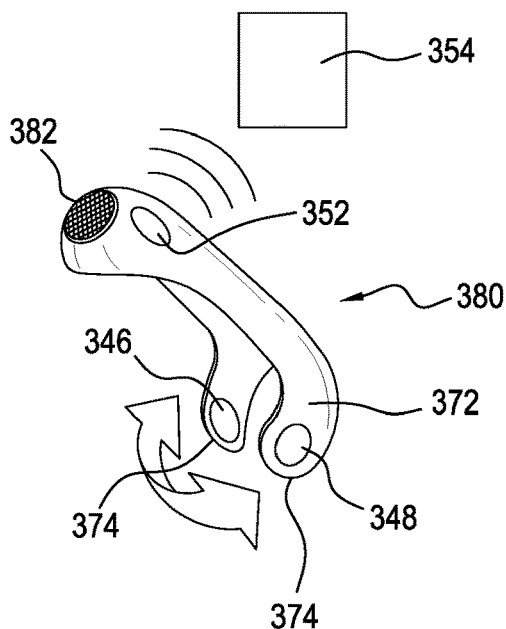
FIG. 46 shows a view of a further thimble-like device in accordance with an exemplary embodiment of the present disclosure.

FIG. 46 shows a view of a further thimble-like device, indicated generally at 380, in accordance with an exemplary embodiment of the present disclosure. Device 380 includes a sensor 382 and a device body 382, which terminates in an open ring configuration 372 at an end opposite from the portion of device body 382 on which sensor 382 is positioned. Device body 382 includes power supply or source 346, electronics 348, and transmitter, receiver, or transceiver 352. Elements of device 360, such as power supply 346 and electronics 348, can be positioned on arms 374 of open ring 372.

Figure 47:
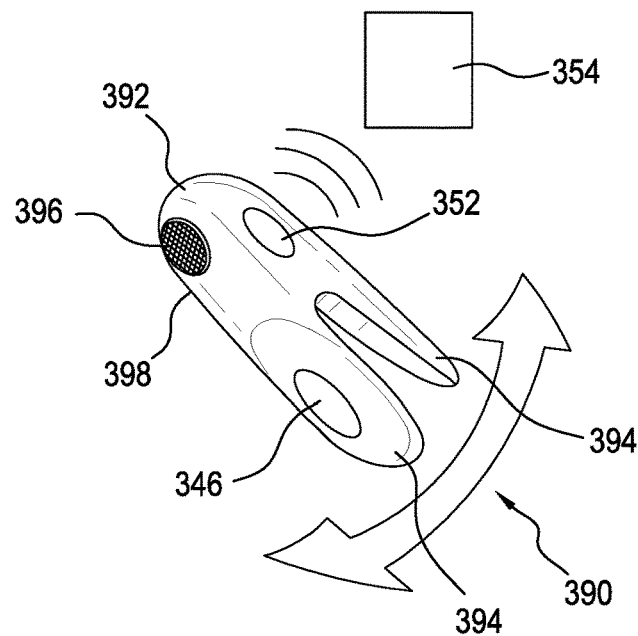
FIG. 47 shows a view of an even further thimble-like device in accordance with an exemplary embodiment of the present disclosure.

Although sensor 362, which can be a contact element or non-contact element, is shown mounted on a tip or end 376 of the thimble-like configurations or glove configurations disclosed herein, it should be understood that sensor 362 can be disposed in or on any portion of the thimble-like configurations or glove configurations including the fingernail area and/or the fingerprint area. For example, FIG. 47 shows a view of an even further thimble-like device, indicated generally at 390, in accordance with an exemplary embodiment of the present disclosure. Device 390 includes a device body 392 and extensions, protrusions, or tongues 394. Device 390 can also include power supply 346 positioned on one extension 394, electronics, including a processor (not shown), and a transmitter 352. Device 390 further includes a sensor 396 positioned on a fingerprint area or portion 398 of device body 392.

Although the embodiments are described as thimble-like for use on a finger, it should be understood that the disclosed embodiments can be used on a wrist, any body part, or any essentially cylindrical or round or circular body part or object. It should be understood that any of the devices disclosed in FIGS. 1 to 46 can be integrated in any of the embodiments of the present disclosure as well as any device described in the present disclosure, and by way of example an emitter-detector pair.

FIG. 48 shows a view of yet an even further thimble-like device, indicated at 410, in accordance with an exemplary embodiment of the present disclosure. Thimble-like device 410 is part of a wearable device system 412, which also includes a wrist-supported device 414 and a cable or wire 416 connecting device 410 to wrist supported device 414. Wrist-supported device 414 can be configured as a watch, and includes a wrist strap or band 418. Wrist supported device includes a power supply 420, a processor 422, a data port 424 to accept an external plug 428, which provides a connection to a cable 430, and a transmitter, receiver, or transceiver 426, which can be described as a communication device, for communication with remote device 354, which can include a cell phone, watch, eyeglasses, tablet, computer, radios, and the like. Though wrist-supported device can include a display as part of a main body, a separate display 432 can also be provided.

FIG. 49 shows a view of still another thimble-like device, indicated at 440, in accordance with an exemplary embodiment of the present disclosure. In this embodiment, two thimble-like devices 440 are included as part of a wearable article system 442, which includes wrist-supported device 444 and a wire or cable 446 that connects wrist-supported device 444 to each thimble-like device 440. In the embodiment of FIG. 49, one thimble-like device 440 dis positioned on an index finger and the other thimble-like device is positioned on a middle finger.

FIGS. 50 and 51 show views of a glove device, indicated generally at 450, in accordance with an exemplary embodiment of the present disclosure. Glove device 450 includes a glove body 452 and two finger extensions 454 extending from glove body 452. The configuration of glove body 452 is such that it provides better hand support than the thimble-like configurations. Each finger extension 454 includes an open bottom area 456 to allow use of the hand in a non-obstructive fashion. Each finger extension 454 includes a sensor 458, which can be the same sensor or different sensors. Glove body 452 includes a wrist support portion 460 having a display 462, a speaker 464, a processor 466, and a power source 468, which thus permits glove device 450 to provide local reporting of data. FIG. 51 shows glove device 450 being operated by the user with sensors 458 positioned on the skin of ABTT terminus 28, though if sensors 458 are non-contact elements, sensors 458 may be positioned adjacent to ABTT terminus 28 a spaced distance from ABTT terminus 28.

FIG. 52 shows a view of another wearable glove device, indicated generally at 470, in accordance with an exemplary embodiment of the present disclosure. Glove device 470 is configured in a standard five finger glove configuration and includes at least two sensors or measuring devices 472, each of which is positioned on a single finger 474 of glove device 470. In the context of this disclosure, single finger 474 should be considered to include a thumb. A third finger 474 of glove device 470 can include another device, such as a light source 476. Glove device 470 further includes a wrist portion 478 on which is positions a display 480, a speaker 482, a processor 484, a power source 486, and a transmitter, receiver, or transceiver 488 configured for communication with remote device 354, which can be, for example, a cell phone, a watch, eyeglasses, a tablet, a computer, radios, and the like.

FIG. 53 shows a view of a further wearable glove device, indicated generally at 490, in accordance with an exemplary embodiment of the present disclosure. Device 490 includes a device body 492, which includes a two finger configuration having two finger extensions 494. Each finger extension is open at a portion of the periphery, which thus enables or allows use of the hand in a non-obstructive fashion. Each finger extension 494 includes a sensor 496 positioned at a distal or tip end thereof. Device body 492 includes a thin wrist portion 498 on or in which are positioned a power source 500, minimal electronics 502 to allow less dense construction, and a transmitter, receiver, or transceiver 504 configured for communication with remote device 354. As with previous embodiments, transceiver 504 is configured for communication remote device 354, which can include, for example, a cell phone, a watch, eyeglasses, a tablet, a computer, radios, and the like. It should be understood that any of the embodiments having more than one sensor can function with only one sensor only one finger extension, and the one sensor and one finger extension are within the scope of the disclosure.

FIGS. 54-57 show views of a wearable ring or ring-like device, indicated generally at 510, in accordance with an exemplary embodiment of the present disclosure. Although device 510 is described as a ring or ring-shaped device, it should be understood that the device of FIG. 54 can include any essentially circular or C-shaped configuration and such configurations are within the scope of the present disclosure. Device 510 includes a device body 512. Device body 512 includes an essentially cylindrical or semi-circular band 514. Device body 512 also includes an extension 516 that can be oriented at a plurality of angles. Positioned on extension 516 is a sensor 518. By positioning extension 516 at a convenient angle, sensor 518 can be positioned near, at, adjacent, alongside, or in contact with ABTT terminus 28, as shown, for example, in FIG. 57. Device body 512 includes a transmitter, receiver, or transceiver 520, a power supply 522, and a processor 524. Transceiver 520 is configured to communicate with remote device 354. Extension 516 is preferably made of an adjustable or flexible material such as plastic with memory or other flexible material, or alternatively includes a hinge mechanism to allow aligning sensor 518 with ABTT terminus 28. FIG. 55 shows ring device 510 being worn on the finger of the user with extension 516 being bent and moved from its original position aligned with the cylindrical or circular shape of device body 512 and positioned on the skin of the finger to a raised position to align with ABTT terminus 28 as shown by dashed lines and as shown in FIG. 57.

FIG. 60 shows a view of an even further ring or ring-like device in accordance with an exemplary embodiment of the present disclosure.

FIG. 58 shows a view of another ring or ring-like device, indicated generally at 530, in accordance with an exemplary embodiment of the present disclosure. Device 530 includes a display 532 and a speaker 534 for local reporting of data, either visually or audibly.

FIG. 59 shows a view of yet another ring or ring or ring-like device, indicated generally at 540, in accordance with an exemplary embodiment of the present disclosure. Device 540 is an extension of the configuration of FIGS. 54-57 included as part of an integral or unitary dual ring configuration that includes a plurality of extensions 516, each of which includes sensor 518 to receive signals or measure two ABTT terminuses simultaneously.

FIG. 60 shows a view of an even further ring or ring-like device, indicated generally at 560 in accordance with an exemplary embodiment of the present disclosure. Device 560 includes a device body 562 being worn on the finger of the user. As with previous embodiments, though not shown, device body 562 includes transceiver, transmitter, or receiver 520, power supply 522, and processor 524. Device body 562 further includes a sliding mechanism 554. Positioned on at least one movable portion of sliding mechanism 554 is a pair of sensors 556. In the exemplary embodiment of FIG. 60, only one portion of sliding mechanism 554 is movable to change a spaced distance or separation between sensors 556 to optimize the spacing of sensors 556 to be able to receive signals from two separated ABTT terminuses 28. In an alternative embodiment, each sensor 556 can be positioned on a movable piece or portion of the sliding mechanism.

Figure 61:
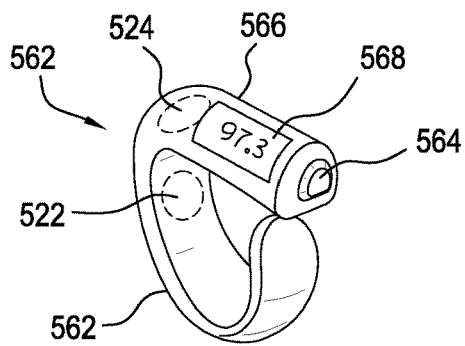
FIG. 61 shows a view of further yet ring or ring-like device in accordance with an exemplary embodiment of the present disclosure.

FIG. 61 shows a view of further yet ring or ring-like device, indicated generally at 560, in accordance with an exemplary embodiment of the present disclosure. Device 560 includes a device body 562 provided with a semicircular, semi-cylindrical, or C-shape. Device 560 includes a sensor 564 positioned on a protrusion 566 that forms a terminal portion of device 560. Device 560 also includes a display 568 for local reporting. Device 560 further includes power source 522 and processor 524.

Figure 62:
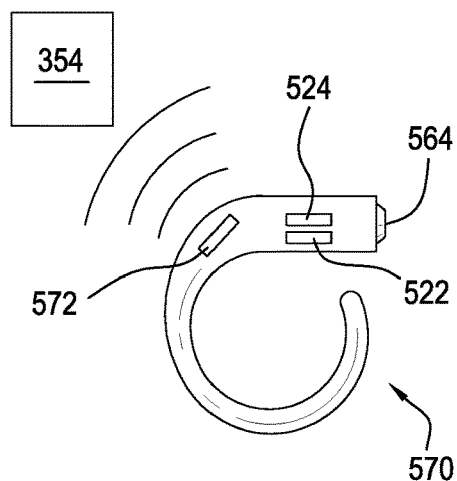
FIG. 62 shows a view of an even further yet ring or ring-like device in accordance with an exemplary embodiment of the present disclosure.
Figure 64:
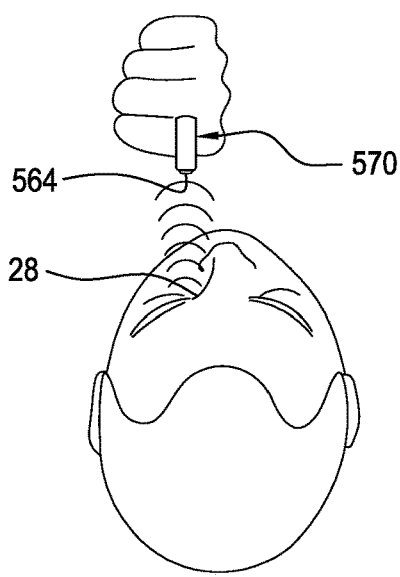
FIG. 64 shows yet another view of the ring or ring-like device of FIG. 62 being operated by the user.
Figure 63:
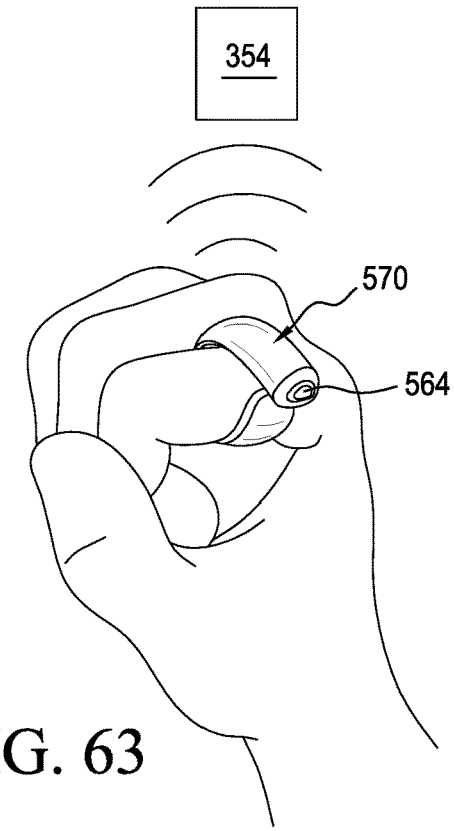
FIG. 63 shows another view of the ring or ring-like device of FIG. 62 being worn on a finger of the user.

FIGS. 62-64 show views of an even further yet ring or ring-like device, indicated generally at 570, in accordance with an exemplary embodiment of the present disclosure. Device 570 is similar to device 560, except display 568 is removed, though it need not be, and a transmitter, receiver, or transceiver 572 for communication with remote device 354 is included. FIG. 63 show device 570 being worn on the finger of the user. FIG. 64 shows another view of device 570 positioned on or adjacent to the face, or nose, of the user, with sensor 564 positioned to be aligned with ABTT terminus 28 and remotely receiving signals or radiation from and/or emitting signals or radiation to ABTT terminus 28.

FIGS. 63 and 64 show views of the ring or ring-like device of FIG. 62 being worn on a finger of the user.

FIG. 64 shows yet another view of the ring or ring-like device of FIG. 62 being operated by the user.

Figure 65:
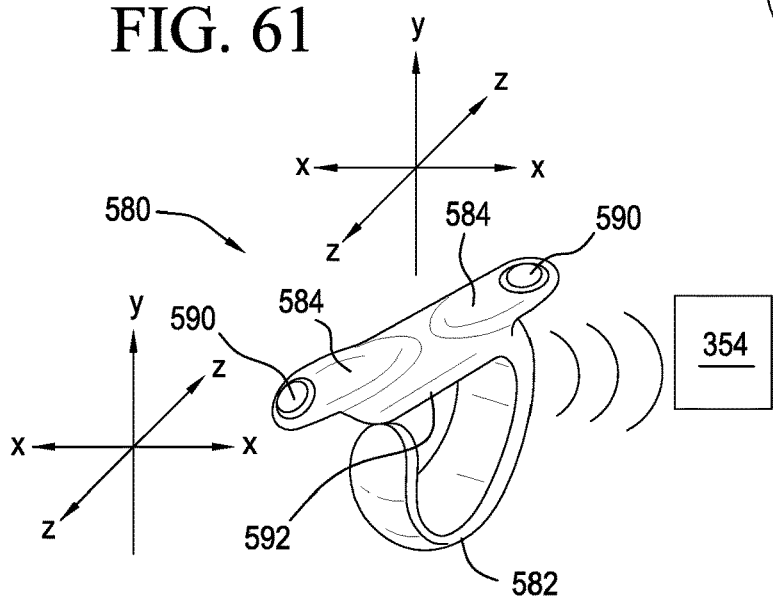
FIG. 65 shows still yet another ring or ring-like device in accordance with an exemplary embodiment of the present disclosure.

FIG. 65 shows still yet another ring or ring-like device, indicated generally at 580, in accordance with an exemplary embodiment of the present disclosure. Device 580 includes a semicircular device body 582. On an upper portion of device body 582 is positioned a plurality of individually slidable or movable slides 584. At a distal or further end 586 of each movable slide 584 is positioned a sensor 590. The spacing or spaced distance between sensors 590 is adjusted by moving movable slides 584 to accommodate variations between individuals. In addition to movable slides 584, device body 582 includes an upper portion 592 that is preferably being made of flexible material that allows adjustment in the X, Y, and Z axes.

Figure 66:
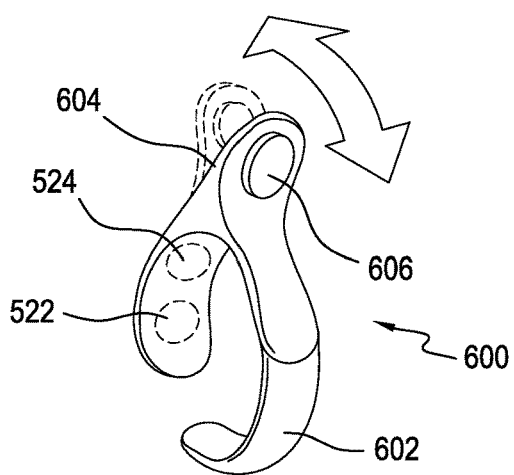
FIG. 66 shows a view of a ring or ring-like device in accordance with an exemplary embodiment of the present disclosure.
Figure 67:
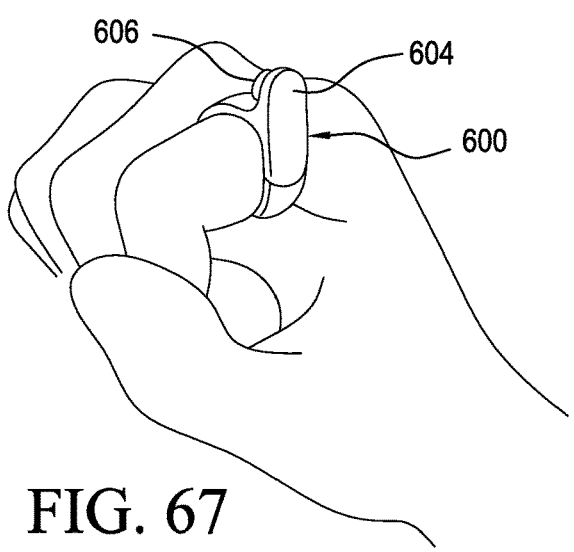
FIG. 67 shows a view of the ring or ring-like device of FIG. 66 being worn on the finger of the user.

FIGS. 66 and 67 show views of a ring or ring-like device, indicted generally at 600, in accordance with an exemplary embodiment of the present disclosure. Device 600 includes a device body 602 that can include any essentially circular, semicircular, cylindrical, or semi-cylindrical, or C-shape configuration. Device body 602 includes a fixed extension 604 of device body 602. Extension 604 includes a sensor 606, which, as has been previously noted multiple times, can be similar to contact elements and non-contact elements described in previous embodiments, and which is positioned thereon. Device 600 also includes power supply 522 and processor 524. Fixed extension 604 is preferably made of an adjustable material such as plastic with memory or other flexible material, or alternatively includes a hinge mechanism to allow aligning sensor 606 with ABTT terminus 28. FIG. 67 shows device 600 being worn on the finger of the user, with fixed extension 604 protruding beyond a plane or upper surface of the finger.

Figure 68:
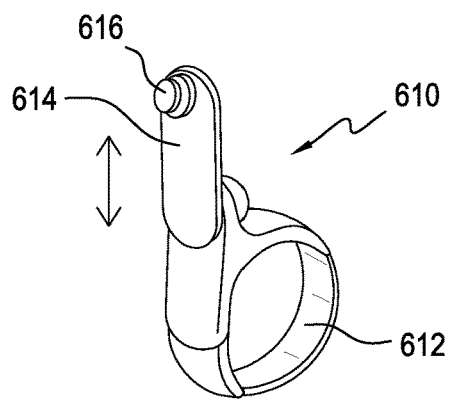
FIG. 68 shows a view of another ring or ring-like device in accordance with an exemplary embodiment of the present disclosure.
Figure 69:
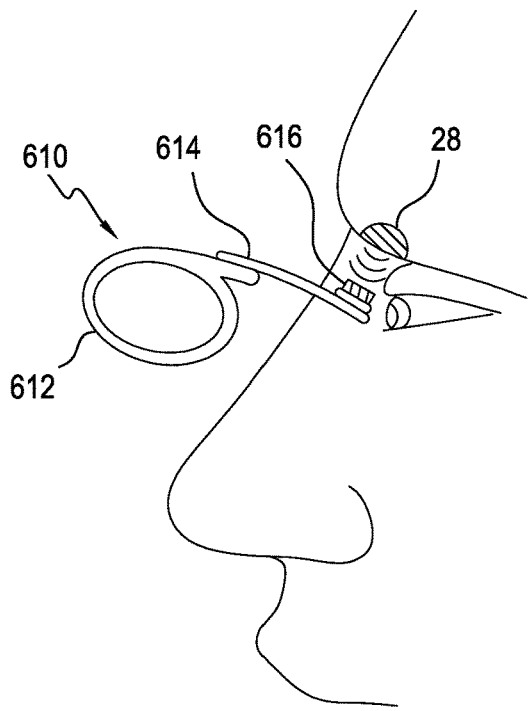
FIG. 69 shows a view of a portion of the ring or ring-like device of FIG. 68 being operated by the user.

FIGS. 68 and 69 show views of another ring or ring-like device, indicated generally at 610, in accordance with an exemplary embodiment of the present disclosure. Device 610 includes a circular or cylindrical device body 612. Device body 612 includes a sliding mechanism 614, which in an exemplary embodiment includes one or more grooves (not shown). Positioned on sliding mechanism 614 is a sensor 616. Sliding mechanism 614 is movable or adjustable to provide refinement of the position of sensor 616 for receiving signals from ABTT terminus 28, which is located in the roof of the eye orbit.

Figure 70:
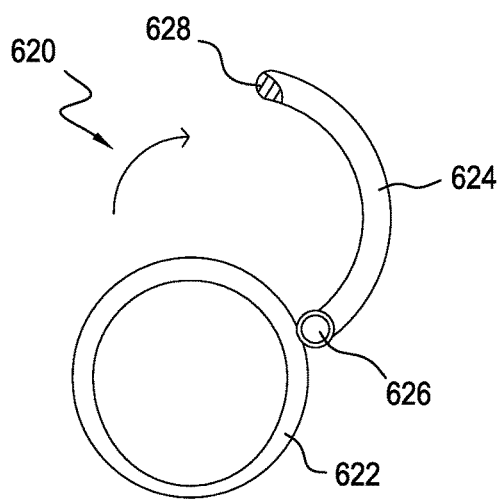
FIG. 70 shows a view of a further ring or ring-like device in accordance with an exemplary embodiment of the present disclosure.
Figure 71:
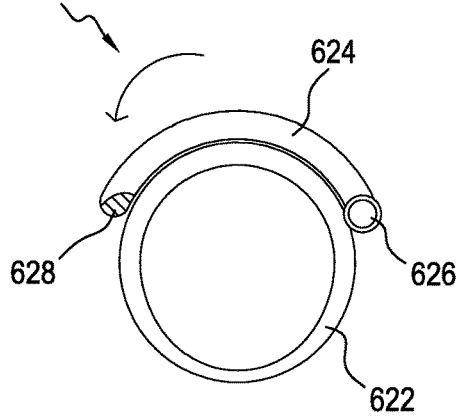
FIG. 71 shows a further view of the ring or ring-like device of FIG. 70.

FIGS. 70 and 71 show views of a further ring or ring-like device, indicated generally at 620, in accordance with an exemplary embodiment of the present disclosure. Device 620 can include any of the elements previously described with respect to other ring or ring-like device embodiments described herein. Device 620 includes a device body 622. Device body 622 includes a curved body lever or extension 624 attached to device body 622 by a hinge 626. Body lever or extension 624 can also be described as a C-shape. Positioned at a distal end or an opposite end of body lever or extension 624 from hinge 626 is a sensor 628 configured to measure signals from ABTT terminus 28. FIG. 70 shows body lever or extension 624 in an opened position, and FIG. 71 shows body lever or extension 624 in a closed position.

Figure 72:
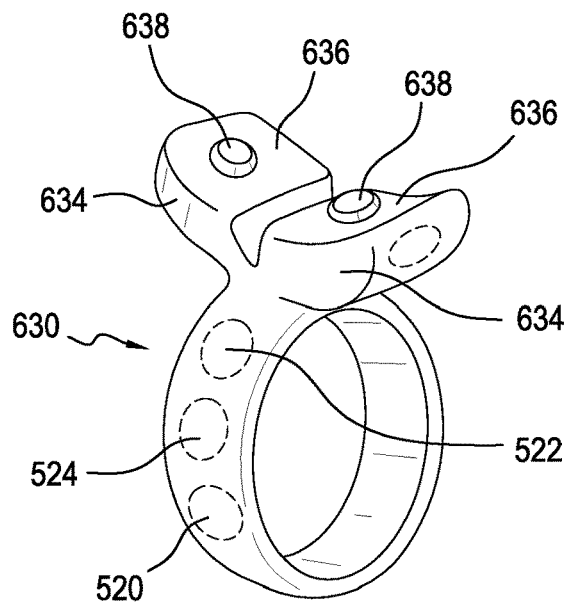
FIG. 72 shows a view of a ring or ring-like device in accordance with an exemplary embodiment of the present disclosure.
Figure 73:
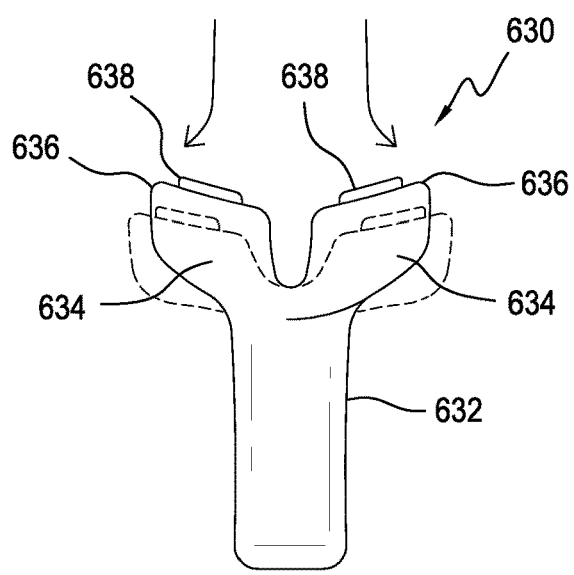
FIG. 73 shows another view of the ring or ring-like device of FIG. 72.
Figure 74:
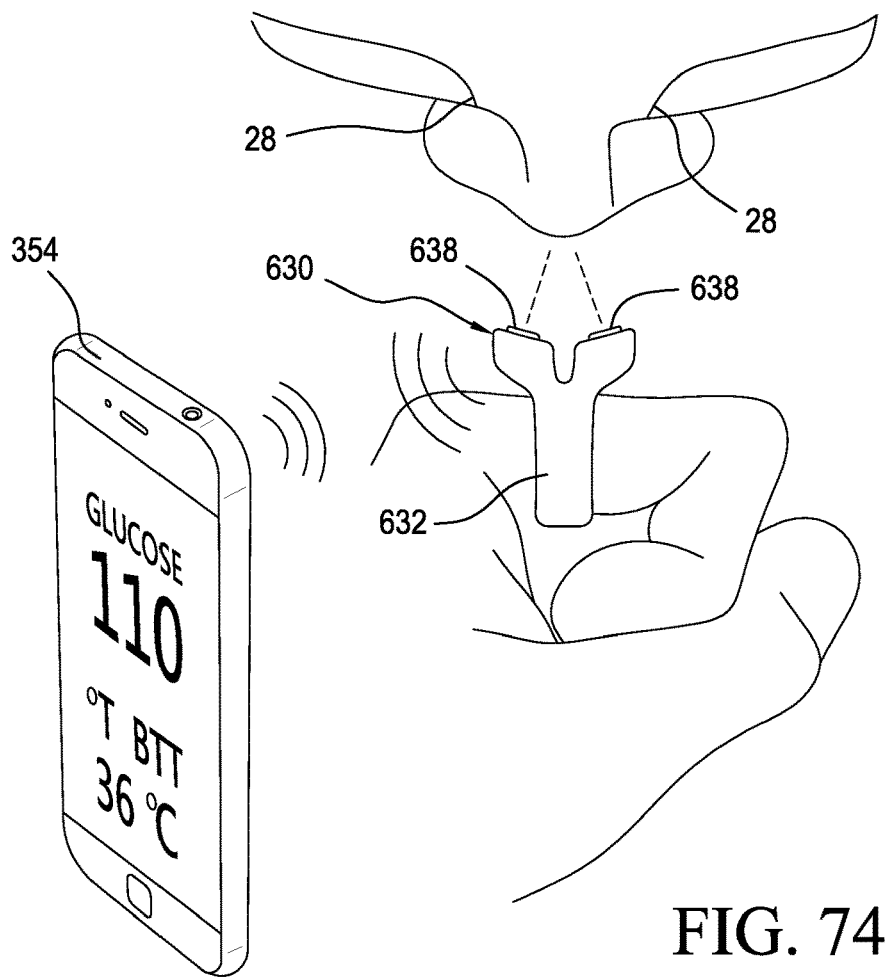
FIG. 74 shows yet another view of the ring or ring-like device of FIG. 72.

FIGS. 72-74 show views of a ring or ring-like device, indicated generally at 630, in accordance with an exemplary embodiment of the present disclosure. Device 630 includes a device body 632. Device body 632 includes a pair of flexible arms 634 that extend in generally opposite directions. Each flexible arm 634 includes a surface 636 that is on an opposite side of flexible arm 634 from device body 632. Positioned on each surface 636 is a sensor 638. Flexible arms 634 are configured to be flexible to permit device body 632 to adjust to the positions of ABTT terminuses 28. Device 630 can include one or more of the elements disclosed in other ring or ring-like device embodiments, including a transceiver, a processor, and a power supply or source.

FIGS. 75-78 show views of a hand supported device, indicated generally at 650, in accordance with an exemplary embodiment of the present disclosure. Device 650 includes a device body 652, which can include a curved surface 654. Device 650 further includes a camera 656, a processor and/or other electronics 658, a power source or supply 660, and a transceiver, transmitter, or receiver 662. Camera 656 can receive and analyze infrared and other signals from ABTT terminus 28. In an exemplary embodiment, curved surface 654 can include a display to assist the user in positioning device 650 for measurement of ABTT terminuses 28. In another exemplary embodiment, curved surface 654 can be reflective, also for assistance in positioning device 650. Device 650 can also include another sensor 664 for measurement of an ABTT terminus 28. As shown in FIG. 77, sensor 664 can be large enough that a portion of sensor 664 protrudes from a back portion 666 of device body 652. To provide for ease of user or operator use, device body 652 can include a handle 668 that extends from back portion 666. Device 650 can also include a display 670 positioned on, for example, an upper portion of back portion 666. Display 670 can be a general display that provides information regarding readings from camera 656 and/or sensor 664.

FIG. 79 shows a view of another device, indicated generally at 680, in accordance with an exemplary embodiment of the present disclosure. Device 680 is similar to device 650, except that handle 668 is replaced by a curved single finger loop 682.

Figure 80:
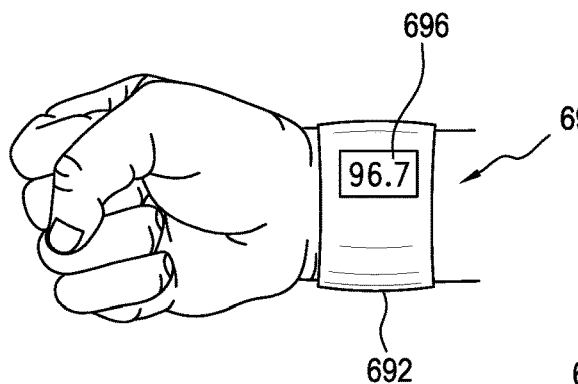
FIG. 80 shows a view of yet another device in accordance with an exemplary embodiment of the present disclosure.
Figure 81:
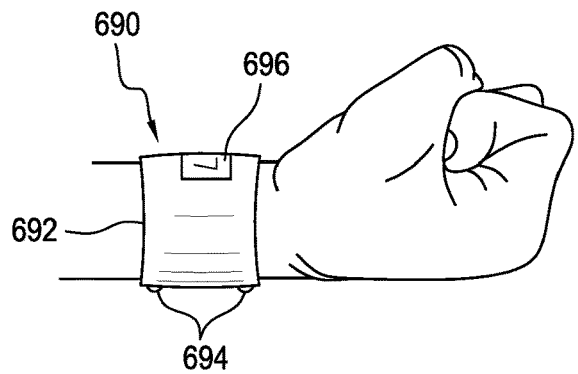
FIG. 81 shows another view of the device of FIG. 80.

FIGS. 80 and 81 show views of yet another wearable device, indicated generally at 690, in accordance with an exemplary embodiment of the present disclosure. Device 690 includes a device body 692, which supports a pair of sensors 694, which may have an adjustable spacing to match the spacing of a pair of ABBT terminuses 28. Device 690 can also include one or more displays 696 for presenting data from sensors 694 locally, or such information can be transmitted via a transceiver or transmitter (not shown) to a separate or remote electronic device 354 for additional processing and/or display. Though not specifically shown, device 690 can include a processor or other electronics and a power supply or source. Device 690 is configured to be supported on a wrist or forearm of the user, such that sensors 694 are positioned on a side of the wrist or forearm that is closer to a patient or subject while display 696 is available or visible to the user.

Figure 82:
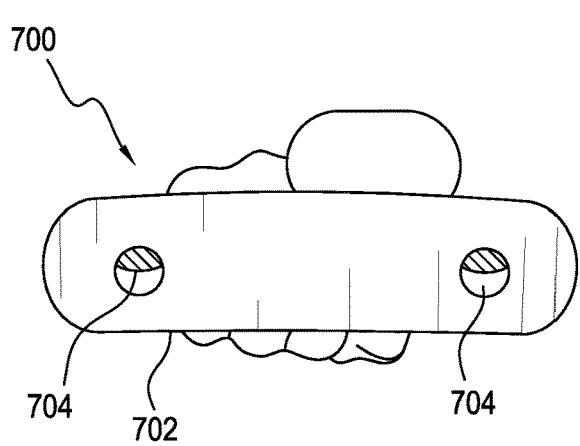
FIG. 82 shows a view of a handheld device in accordance with an exemplary embodiment of the present disclosure.
Figure 83:
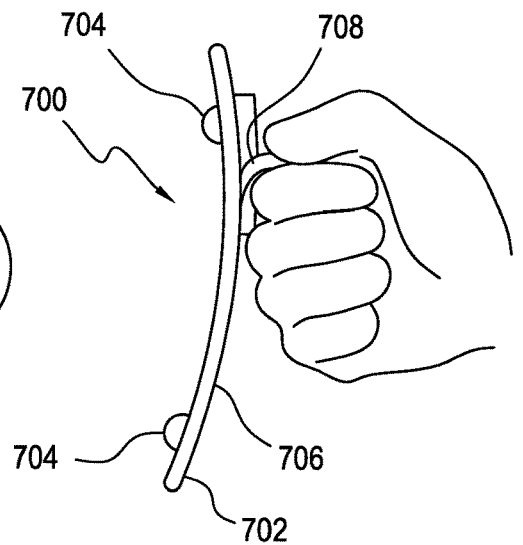
FIG. 83 shows another view of the device of FIG. 82.
Figure 84:
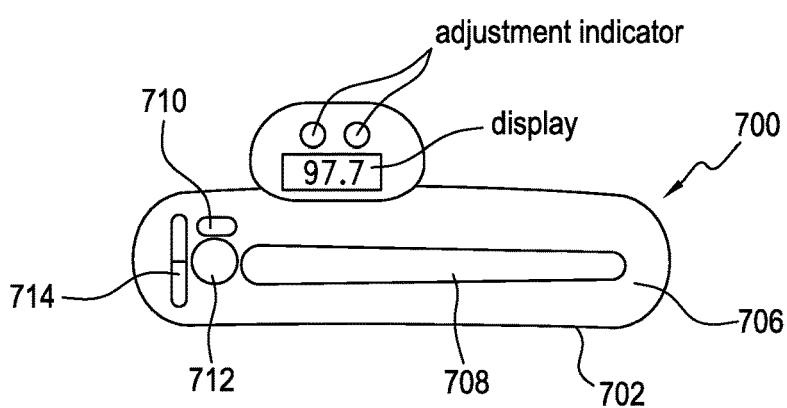
FIG. 84 shows yet another view of the device of FIG. 82.

FIGS. 82-84 show views of a handheld device, indicated generally at 700, in accordance with an exemplary embodiment of the present disclosure. Device 700 includes a device body 702, which supports a pair of adjustable sensors 704 positioned a spaced distance apart to approximately match adjustable sensors 704 with a field of view of sensors 704. Adjustability of sensors 704 can be via angle to modify a field of view, or can be by a sliding mechanism (not shown). Sensors 704 can be any of the sensors described elsewhere herein for measurement of signals from ABTT terminus 28. Extending from a back portion 706 of device body 702 is a hand support 708, such as a handle or a finger loop. Device 700 can also include various controls for operation of sensors 704, such as a reset switch 710, an adjustment switch 712 to provide for field of view or sliding adjustments, and a left/right sensor switch 714, which permits selecting one of sensors 704 for position adjustment. Back portion 706 can also support a display 716 and an adjustment indicator 718, which provides an indication of when alignment with left and/or right ABTT terminus 28 is achieved. Such indication can be based, for example, on locating a temperature within a predetermined range indicative of ABTT terminus 28. Such indication can be variable to indicate proximity to ABTT terminus 28. For example, if the predetermined temperature is 97 degrees Fahrenheit, a red color can represent less than 90 degrees Fahrenheit, an orange color can represent a range of 90-93 degrees Fahrenheit, a yellow color can represent a range of 93-95 degrees Fahrenheit, a pale green color can represent a range of 95 to 97 degrees Fahrenheit, and a bright green color can represent a temperature greater than 97 degrees Fahrenheit. As with other embodiments disclosed herein, device 700 can includes a power source or supply, a processor and/or other electronics, and a transceiver, transmitter, or receiver.

It should be understood that all measurements described herein are measurements of parameters. Though such measurements can occur at ABTT terminus 28, they can occur in other locations. In addition, it should be understood that while these parameters can be measured at the surface of the skin, those parameters can represent conditions internal to the body, as explained herein.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. A wearable article, comprising:
  a device body configured to be supported entirely on a finger of a user, the device body including an opening at a first end sized and dimensioned for insertion of the finger, and a distal end on an opposite end of the device body from the opening;
  a power supply positioned on the device body;
  a removably mounted output element positioned in the distal end of the device body at a fingertip, the removably mounted output element positioned offset from a centerline of the wearable article toward an upper side of the finger of the user, the removably mounted output element being a non-contact output element and the removably mounted output element being configured to be spaced from a brain thermal tunnel terminus located between an upper eyelid and eyebrow when measuring thermal parameters of the brain thermal tunnel terminus, the output element configured to:
    receive power from the power supply, and
    to deliver an output to skin other than that of the user's finger at the brain thermal tunnel terminus, the output element being located at least partially in a recess in the distal end of the device body; and
  a communication device positioned on the device body and configured to receive a signal from a separate electronic device and to use the signal to control the output element with respect to the brain thermal tunnel terminus.

2. The wearable article of claim 1, wherein the output element is interchangeable with other output elements different from the output element.

3. The wearable article of claim 1, wherein the separate electronic device is one of a watch, a laptop, a tablet, and a cell phone.

4. A wearable article, comprising:
  a device body configured to be supported entirely on a finger of a user, the device body including an interior space sized and dimensioned to accept the finger inserted from a first end of the device body, the interior space extending along the device body from the first end toward a second, opposite end of the device body and terminating internal to the device body;
  a power supply positioned on the device body;
  a removably mounted input element positioned on the device body at the second, opposite end of the device body at a fingertip, the removably mounted input element positioned offset from a centerline of the wearable article toward an upper side of the finger of the user, the removably mounted input element being a non-contact input element and the removably mounted input element being configured to be spaced from a brain thermal tunnel terminus located between an upper eyelid and eyebrow when measuring thermal parameters of the brain thermal tunnel terminus, and oriented to receive an input from a direction opposite from the first end, the input element configured to: receive power from the power supply, to measure a parameter of skin other than that of the user's finger at the brain thermal tunnel terminus, and to transmit a signal representing the measured parameter, the input element being located at least partially in a recess in the second end of the device body; and
  a communication device positioned on the device body and configured to receive the signal and to transmit the signal to a separate electronic device.

5. The wearable article of claim 4, wherein the input element is interchangeable with other input elements different from the input element.

6. The wearable article of claim 4, wherein the separate electronic device is one of a watch, a laptop, a tablet, and a cell phone.

7. A wearable article, comprising:
  a device body configured to be supported entirely by a finger, the device body including a finger opening at a first end;
  a power supply positioned on the device body;
  a combination removably mounted input and output element positioned on the device body at a fingertip, the removably mounted input and output element positioned offset from a centerline of the wearable article toward an upper side of the finger of the user, the removably mounted input and output element being a non-contact input and output element, the removably mounted input and output element being configured to be spaced from a brain thermal tunnel terminus located between an upper eyelid and an eyebrow when measuring thermal parameters of the brain thermal tunnel terminus, a second end that is opposite from the first end, the removably mounted input and output element configured to:

receive power from the power supply, to provide at least one output to skin other than that of the user's finger, to measure a parameter of the skin other than that of the user's finger, and to transmit a signal representing the measured parameter, the input and output element being located at least partially in a recess in the second end of the device body; and a communication device positioned on the device body and configured to receive the signal from the brain thermal tunnel terminus and to transmit the signal to a separate electronic device.

8. The wearable article of claim 7, wherein the combination input and output element is interchangeable with other combination input and output elements different from the combination input and output element.

9. The wearable article of claim 8, wherein the other combination input and output elements includes one of a combination needle and glucose meter strip, a combination radio frequency emission and radio frequency detection device, a combination emission and detection device, and a combination thermal transfer and blood pressure sensing device.

10. The wearable article of claim 7, wherein the separate electronic device is one of a watch, a laptop, a tablet, and a cell phone.

* * * * *